(12) United States Patent
Joshi et al.

(10) Patent No.: US 11,694,344 B2
(45) Date of Patent: Jul. 4, 2023

(54) SYSTEM AND METHOD FOR AUTOMATED CELL POSITIONING

(71) Applicant: Thread Robotics Inc., San Jose, CA (US)

(72) Inventors: Kiran Joshi, San Jose, CA (US); Gregory Burd, San Jose, CA (US)

(73) Assignee: Thread Robotics Inc., San Jose, CA (US)

( * ) Notice: Subject to any disclaimer, the term of this patent is extended or adjusted under 35 U.S.C. 154(b) by 0 days.

(21) Appl. No.: 17/981,872

(22) Filed: Nov. 7, 2022

(65) Prior Publication Data

US 2023/0144306 A1 May 11, 2023

Related U.S. Application Data

(60) Provisional application No. 63/276,366, filed on Nov. 5, 2021, provisional application No. 63/309,427, filed on Feb. 11, 2022, provisional application No. 63/397,622, filed on Aug. 12, 2022.

(51) Int. Cl.
*G06T 7/246* (2017.01)
*G06T 7/73* (2017.01)
*C12N 5/073* (2010.01)

(52) U.S. Cl.
CPC ............ *G06T 7/248* (2017.01); *C12N 5/0604* (2013.01); *G06T 7/73* (2017.01); *G06T 2207/10016* (2013.01); *G06T 2207/10056* (2013.01); *G06T 2207/20081* (2013.01)

(58) Field of Classification Search
CPC ......... G06T 7/0012; G06T 7/20; G06T 7/246; G06T 7/248; G06T 7/70; G06T 7/73; G06T 7/97; G06T 2207/30024; G06V 20/69; G06V 20/695; G06V 20/698; C12N 5/0604; C12N 5/061; C12N 5/0612
See application file for complete search history.

(56) References Cited

U.S. PATENT DOCUMENTS

| 10,510,143 | B1 | 12/2019 | Zhou et al. |
| 10,977,477 | B2 | 4/2021 | Shafiee .............. G06K 9/00127 |
| 2006/0257909 | A1 | 11/2006 | Harton et al. ..................... 435/6 |
| 2009/0029471 | A1 | 1/2009 | Palacios-Boyce |
| 2011/0092762 | A1 | 4/2011 | Wong et al. |

(Continued)

FOREIGN PATENT DOCUMENTS

| WO | WO-2015/153691 A2 * | 10/2015 | ........... G06K 9/0014 |
| WO | 2018152157 A1 | 8/2018 | |

(Continued)

OTHER PUBLICATIONS

"Machine translation of 20200909471", via Google Patents, 38 pages. (Year:2022).

(Continued)

*Primary Examiner* — Andrew W Johns
(74) *Attorney, Agent, or Firm* — Jeffrey Schox; Diana Lin

(57) ABSTRACT

The method for automated cell positioning can include: sampling a video of a scene having a gamete, tracking the gamete, and positioning the gamete within a target region. The method can optionally include: determining attribute values for the gamete, selecting the gamete, reorienting the gamete, and/or manipulating the gamete, and/or any suitable steps.

20 Claims, 21 Drawing Sheets

(56) References Cited

U.S. PATENT DOCUMENTS

| | | | |
|---|---|---|---|
| 2017/0089820 A1 | 3/2017 | Wong et al. | ............ G01N 15/10 |
| 2017/0109879 A1 | 4/2017 | Urbano et al. | ......... G06T 7/0012 |
| 2018/0330510 A1 | 11/2018 | Watanabe | ................ G06T 7/251 |
| 2018/0348114 A1 | 12/2018 | Hsu et al. | .......... G01N 15/1475 |
| 2019/0120750 A1 | 4/2019 | Kim | |
| 2019/0302093 A1 | 10/2019 | Hsu et al. | |
| 2020/0226750 A1 | 7/2020 | Shafiee et al. | |
| 2020/0311916 A1 | 10/2020 | Tran | |
| 2020/0399593 A1 | 12/2020 | Subirán Ciudad et al. | |
| 2021/0319208 A1* | 10/2021 | Ohara et al. | ............ G02B 21/32 |

FOREIGN PATENT DOCUMENTS

| | | | |
|---|---|---|---|
| WO | 2020090947 A1 | 5/2020 | |
| WO | 2020198779 A1 | 10/2020 | |
| WO | 2021144800 A1 | 7/2021 | |
| WO | 2021200003 A1 | 10/2021 | |

OTHER PUBLICATIONS

"Machine translation of WO2021200003", via Google Patents, 20 pages (Year:2022).

"Priority document JP2020-063284 to WO2021/20003A1", filed Mar. 25, 2021, 41 pages.

"WHO laboratory manual for the Examination and processing of human semen Fifth Edition", World Health Organization Jun. 2021.

Ben-Yehuda, Keren , et al., "Simultaneous Morphology, Motility and Fragmentation Analysis of Live Individual Sperm Cells for Male Fertility Evaluation", Advanced Intelligent Systems, vol. 4, Issue 4, 12 pages, Dec. 26, 2021, https://onlinelibrary.wiley.com/doi/10.1002/aisy.202100200.

Butola, Ankit , et al., "High Spatially sensitive quantitative phase imaging assisted with deep neural network for classification of human spermatozoa under stressed condition", Scientific Reports, Aug. 4, 2020, vol. 10, 12 pages.

Chang, Violeta , et al., "Gold-standard for computer-assisted morphological sperm analysis", Computers in Biology and Medicine, Apr. 1, 2017, vol. 83, pp. 143-150.

Dai, Changsheng , et al., "Automated motility and morphology measurement of live spermatozoa", American Society of Andrology and European Academy of Andrology, 2021;00:1-9.

Leung, Clement , "Robotic Single Cell Manipulation for Biological and Clinical Applications", Thesis, 2011, University of Toronto, 98 pages, https:www.bac-lac.gc.ca/eng/services/thesis/Pages/item.aspx?idNumber=1032903771.

McCallum, Christopher , et al., "Deep learning-based selection of human sperm with high DNA integrity", Communications Biology (2019)2:250.

Valiuskaite, Viktorija , et al., "Deep Learning Based Evaluation of Spermatozoid Motility for Artificial Insemination", Sensors 2021, 21, 72.

Wang, Yihe , et al., "Prediction of DNA Integrity from Morphological Parameters Using a Single-Sperm DNA Fragmentation Index Assay", Adv. Sci. 2019, 6, 1900712.

You, Jae Bem , et al., "Machine learning for sperm selection", Nature Review Urology vol. 18, Jul. 2021.

Yuzkat, Mecit , et al., "Multi-model CNN fusion for sperm morphology analysis", Computers in Biology and Medicine, vol. 137, 12 pages, Aug. 24, 2021.

\* cited by examiner positioning system at position 1 positioning system at position 2

SYSTEM AND METHOD FOR AUTOMATED CELL POSITIONING

CROSS-REFERENCE TO RELATED APPLICATIONS

This application claims the benefit of U.S. Provisional Application No. 63/276,366 filed 5 Nov. 2021, U.S. Provisional Application No. 63/309,427 filed 11 Feb. 2022, and U.S. Provisional Application No. 63/397,622 filed 12 Aug. 2022, each of which is incorporated in its entirety by this reference.

TECHNICAL FIELD

This invention relates generally to the cell manipulation field, and more specifically to a new and useful system and method in the cell positioning field.

DETAILED DESCRIPTION

The following description of the embodiments of the invention is not intended to limit the invention to these embodiments, but rather to enable any person skilled in the art to make and use this invention.

1. Overview

Figure 1:
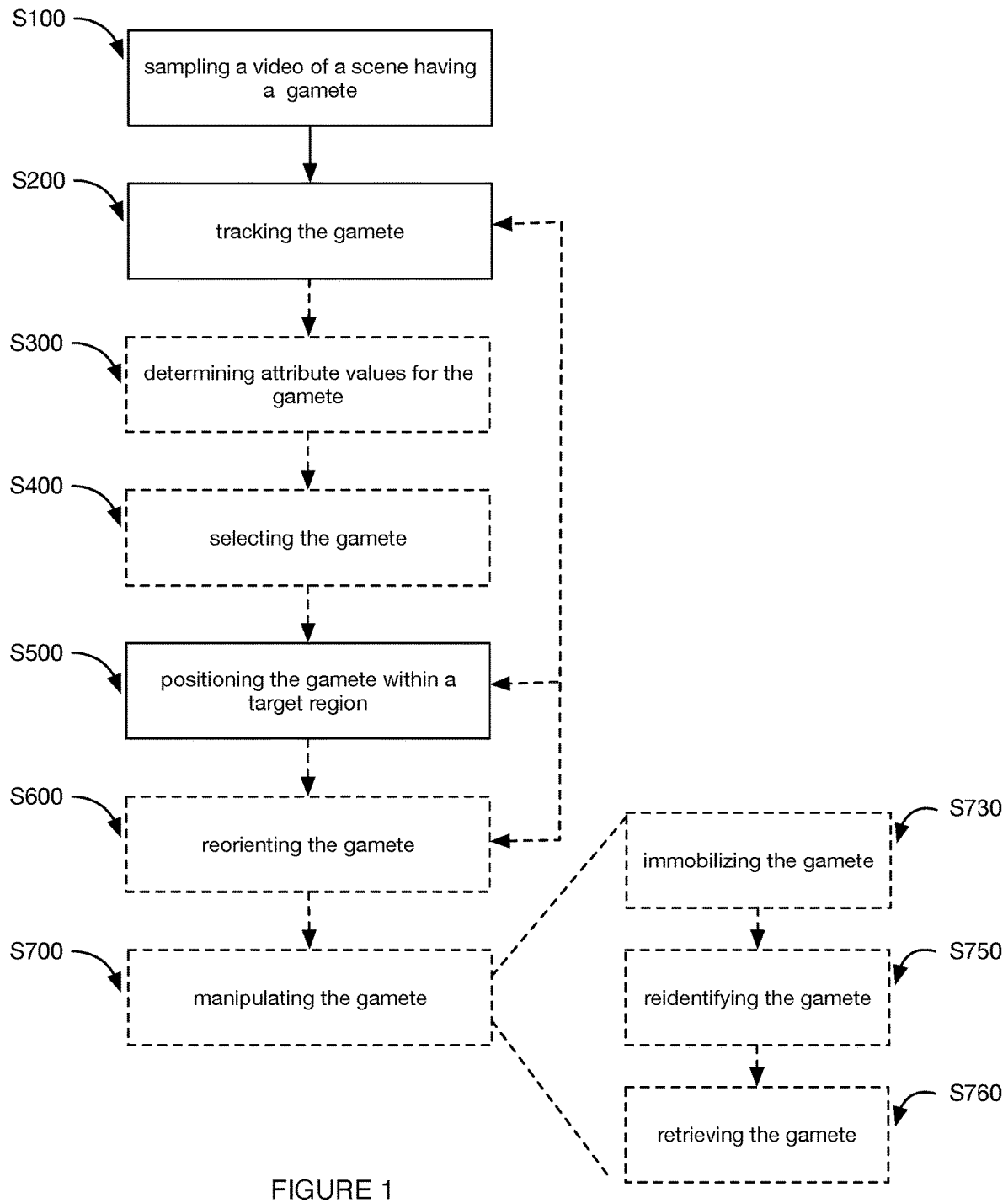
FIG. 1 is a schematic representation of a variant of the method.

As shown in FIG. 1, the method can include: sampling a video of a scene having a gamete S100; tracking the gamete S200; and positioning the gamete within a target region S500. The method can optionally include: determining attribute values for the gamete S300; selecting the gamete S400; reorienting the gamete S600; manipulating the gamete S700; and/or any other suitable steps.

In variants, the method can function to facilitate the tracking and/or manipulation of a moving gamete.

2. Examples

In an example, a spermatozoon can be selected from a population of sperm (e.g., a petri dish of sperm) for tracking and retrieval. In a specific example, for each of a set of sperm in the population, attribute values can be extracted from a video of the respective sperm, wherein a target sperm can be automatically selected based on the attribute values. The system tracks the physical location of the target sperm throughout the dish using a first tracking model, and automatically (e.g., continuously, iteratively, periodically, etc.) moves a positioning system (e.g., an actuated platform on a microscopy stage, an actuated platform separate from the microscopy stage, the stage itself, etc.) to keep the sperm within a target region (e.g., near the center of a field of view) and within focus. A manipulation system (e.g., an intracytoplasmic sperm injection (ICSI) or intracytoplasmic morphologically selected sperm injection (IMSI) needle and/or micropipette, an aspirator, etc.) can optionally physically contact the sperm and/or move fluid near the sperm to reorient the sperm to a predetermined pose prior to immobilization. The manipulation system can then immobilize the target sperm, such as by pinning the sperm to the dish and swiping across the sperm tail. The target sperm can then be reidentified in the dish after immobilization (e.g., after the manipulation system moved the target sperm during immobilization) and retrieved using the same or a different manipulation system. In a specific example, the first tracking model tracks the sperm through the dish, pre-immobilization, based on motion features of the sperm, while the target sperm can be reidentified (e.g., after an immobilization attempt) by using a second tracking model based on appearance features of the sperm. In examples, sperm retrieval can be verified visually (e.g., based on whether the allegedly retrieved sperm moves with the manipulator, whether the sperm is moving along the manipulator at an expected speed and/or direction) and/or otherwise verified.

In variations, for a container with multiple cells (e.g., multiple gametes, multiple cell types, etc.), a plurality of cells can be detected and labeled with their attribute values. The user can input a cell type, attribute value range, score based on attribute values, and/or any other selection criteria. Cells which satisfy the selection criteria can then be automatically: tracked, positioned within an immobilization region, reoriented within a target orientation range (e.g., substantially orthogonal to the bore of an aspirator), immobilized (e.g., via the aspirator), reidentified, repositioned within a target retrieval region, and retrieved (e.g., via the aspirator).

3. Technical Advantages

Variants of the technology can confer one or more advantages over conventional technologies.

First, variants of the technology can iteratively track and position gametes within a target region in real-time. In an example, this tracking and positioning can be particularly useful for a high-density gamete population that appears homogeneous (e.g., under magnification) to the naked eye (e.g., in which manually tracking a gamete would be difficult), but exhibits differentiating attribute values (e.g., microscopic appearance differences, motion-based differences, etc.). In a specific example, conventional gamete tracking methods are unable to track the same target gamete both pre-immobilization (e.g., while the gamete is motile) and post-immobilization (e.g., wherein the gamete moved during immobilization and needs to be relocated). In variants, the technology can include determining motility and appearance features for a target gamete pre-immobilization, tracking the target gamete based on the motility features, and re-identifying the target gamete post-immobilization using the appearance features (e.g., for an unmodified region of the gamete, such as the head).

Second, in variants, the technology can automatically reorient a gamete (e.g., rotate the gamete relative to an imaging system). This reorientation can provide the advantage of positioning the gamete in a more ergonomic, safer (e.g., less likely to injure the gamete head), and/or more effective pose for gamete manipulation (e.g., including sperm immobilization). In a specific example, the method can reorient the gamete without touching the gamete head.

Third, in variants, the technology can improve the efficiency and accuracy of gamete manipulation by a user. In an example, maintaining the position of the gamete within a target region can enable faster and more accurate immobilization and retrieval, since the user does not need to manually manipulate the stage, cell container, and/or the imaging focus range while immobilizing or retrieving the gamete.

Fourth, variants of the system and method can drastically increase throughput and accuracy by automating the process of gamete selection, physical gamete tracking, gamete immobilization, and/or gamete retrieval. In an example, this automation can enable the selection and retrieval of gametes in the absence of a local expert (e.g., an embryologist can remotely select a gamete for the system to automatically retrieve and/or the system can be trained based on previous expert selection to automatically select the gamete). This automation can further improve the scalability of the gamete selection and retrieval process.

However, further advantages can be provided by the system and method disclosed herein.

4. System

Figure 2:
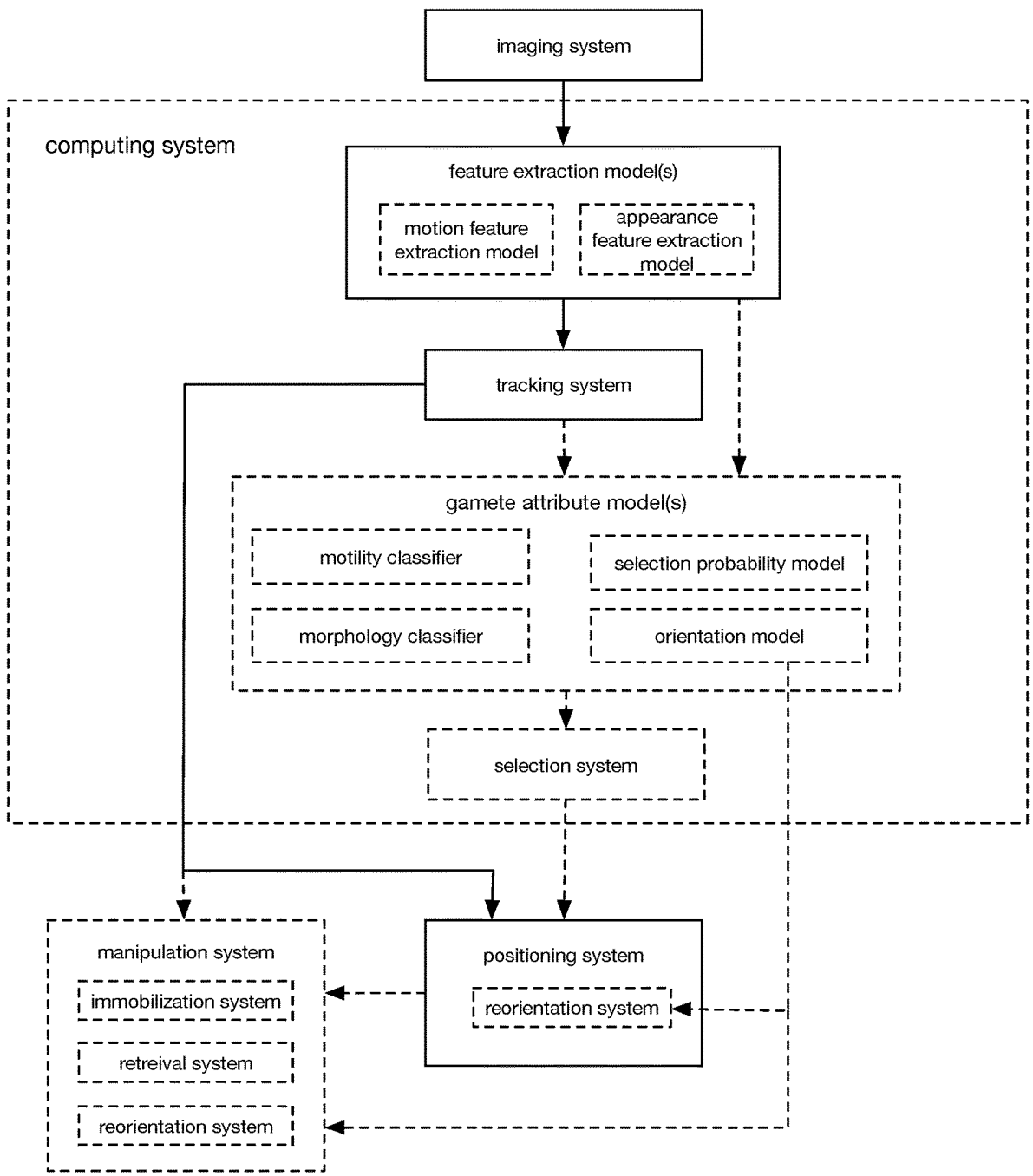
FIG. 2 is a schematic representation of a variant of the system.

The method can be performed using a system including one or more: imaging systems, tracking systems, computing systems, manipulation systems (e.g., immobilization system, retrieval system, reorientation system, etc.), positioning systems, and/or any other suitable systems. The system can optionally include one or more: selection systems, specialist sets, and/or any other suitable systems. An example of the system is shown in FIG. 2.

The imaging system is preferably an optical microscopy system, but can be any other suitable system. The imaging system can include a bright-field microscope, confocal microscope, phase contrast microscope, DIC microscope, and/or any other microscope. The imaging system can include one or more cameras (e.g., monocular cameras, stereo cameras, CCD cameras, CMOS cameras, multi- or hyper-spectral cameras, etc.). The camera can optionally be modified to interface with a microscope. The camera resolution is preferably selected such that each gamete is represented by at least 50 px, 75 px, 100 px, and/or 150 px, a range or value therein, but can alternatively be higher or lower. The resolution of the resultant image can be: 4 Mpixels, 8 Mpixels, 12 Mpixels, 16 Mpixels, 24 Mpixels, 36 Mpixels, 44 Mpixels, and/or have another resolution. The camera pixel size can be between 1 μm2-25 μm2 or any range or value therebetween (e.g., 1 um×1 um, 2.75 um×2.75 um, 4 um×4 um, etc.), but can alternatively be less than 1 μm2 or greater than 25 μm2. The camera pixel shape can be square, rectangular, and/or any other shape. The imaging system field of view can be: larger, smaller, equal to, and/or otherwise related to the extent of a scene. The scene can be defined by a slide, petri dish, tray, well, vial, workspace, and/or other cell container. The imaging system can acquire images at 10, 15, 20, 25, 30, 35, 40, 50, 60, 70, 80, 90, 100 frames per second, any range therein, and/or any other frame rate suitable for the gametes (e.g., moving at approximately 25 microns per second). Data acquired by the imaging system can be downsampled (e.g., downsampling the frame resolution for input to the tracking system, downsampling the framerate for morphology attribute value determination, etc.), stitched (e.g., to form a larger frame), cropped (e.g., from full-frame to partial-frame), and/or otherwise processed. However, the imaging system can be otherwise configured.

The tracking system can function to identify and/or track gametes across video frames. Gametes can be tracked across time (e.g., across successive frames of a video) and/or spatially (e.g., in physical space across the scene). The tracking system is preferably digital, but can additionally or alternatively be physical (e.g., interfacing with the positioning system to keep the gamete in the field of view). The tracking system can include and/or interface with one or more models (e.g., gamete detection models, tracking models, motion models, appearance models, feature extraction models, etc.), a computing system (e.g., local to the imaging system, remote from the imaging system, distributed, etc.), and/or any other suitable system or module. In a specific example, gamete detection can be performed using a first computing system (e.g., with a GPU), and gamete tracking can be performed using a second computing system (e.g., wherein the second computing system can interface with the positioning system, the manipulation system, the first computing system, and/or any other system). The first and second computing systems can be connected using Wi-Fi, Bluetooth, I2c, SPI, Ethernet, and/or any other networking and/or connection methods. Optionally, one or more components of the imaging system, scene, positioning system, manipulation system, and/or any other system component can be actuated based on the tracking system output (e.g., based on a gamete track). However, the tracking system can be otherwise configured.

The positioning system can function to move a gamete to a target pose (e.g., target position and orientation), target region (e.g., a target position within a region), a target orientation, and/or to any other suitable target spatial arrangement. In specific examples, the positioning system functions: to maintain focus of the imaging system on the gamete; to spatially track the gamete across the scene (e.g., when the field of view is less than the scene size), thus ensuring the gamete remains within the field of view and/or at the center of the field of view; to prepare the gamete for manipulation by the manipulation system (e.g., repositioning and/or reorienting the gamete to facilitate immobilization and/or retrieval); and/or provide any other functionality.

The target region, target position, and/or target orientation can be determined relative to: the field of view, the manipulation system, the imaging system, the scene, and/or be otherwise configured. In examples, the target region can be: a field of view, a region within a field of view (e.g., within a predetermined 2D or 3D region under a microscope or camera lens, within focus limits, etc.), a focus region (e.g., a region where the gamete and/or a portion of the gamete is within focus for the imaging system), a manipulation region (e.g., a region where the manipulation system can reorient, immobilize, and/or retrieve the gamete), a target subregion, and/or any other region. The target region can be smaller than the scene, the size of the scene, or larger than the scene. The target position can optionally be a location within the target region (e.g., a set of coordinates at or near the center of the target region). In an example, the target orientation can be a manipulation orientation (e.g., an orientation where the manipulation system can immobilize and/or retrieve the gamete). The target region, position, and/or orientation can be determined: manually; determined based on the workspace of the manipulation system (e.g., range of positions accessible by the manipulation system, etc.); determined based on the range of orientations accessible by the manipulation system; and/or otherwise determined.

The positioning system and/or one or more components therein can be actuated in 1D, 2D, 3D, 4D, 5D, 6D, and/or any number of dimensions. In a first specific example, the positioning system can be actuated in three dimensions (e.g., x, y, and z actuation), wherein gamete rotation can optionally be performed by a user, by the manipulation system, and/or by any other suitable system. In a second specific example, the positioning system can be actuated in four dimensions (e.g., x, y, and z actuation and rotation). In a third specific example, the positioning system can be actuated in six dimensions (e.g., x, y, z, yaw, pitch, and roll actuation).

The positioning system and/or one or more components therein can be automatically actuated, manually actuated, and/or stationary. The positioning system actuation can be based on: actuation instructions, a user (e.g., manual inputs from a user), and/or any otherwise determined.

The positioning system can be: the imaging system and/or part of the imaging system, connected to the imaging system, not part of and/or connected to the imaging system, and/or otherwise arranged relative to any other system. The positioning system can move: the stage, the objective lens, the cell container (e.g., the dish, independent of the stage), the gamete, and/or any other suitable component. In a first variant, the positioning system includes the imaging system and/or interfaces directly with the imaging system. For example, the positioning system can include actuators moving: an imaging system stage, the objective lens, a focus knob adjusting the objective lens, a camera, and/or any other component of the imaging system. In a second variant, the positioning system is separate and/or distinct from the imaging system. In examples, the positioning system includes an actuated platform separate from the imaging system stage, an actuated platform mounted to the imaging system stage, any actuated stage (e.g., xy stage, xyz stage, xyz stage with rotational actuation, etc.), the cell container, and/or any other actuated system. In a third variant, the positioning system includes a first system separate from the imaging system and a second system connected to and/or a part of the imaging system. In a first example, the positioning system includes imaging system stage actuation as well as a separate actuated platform (e.g., imaging system stage actuation for xyz motion and a separate actuated platform for rotation; coarse xyz actuation from the imaging system stage and fine xyz actuation from a separate actuated platform; etc.). In a second example, the positioning system includes an imaging system focus actuation (e.g., actuating the z-direction of the imaging system stage, actuation of an objective lens, otherwise adjusting the focus, etc.) as well as a separate actuated platform (e.g., for xy actuation). The positioning system can optionally be retrofit on an existing imaging system (e.g., to motorize the imaging stage movement and/or the focus adjustment) and/or constructed separately (e.g., an actuated platform resting on the imaging stage, an actuated platform mounted separately from the imaging stage, etc.).

The positioning system can be: the manipulation system and/or part of the manipulation system, connected to the manipulation system, not part of and/or connected to the manipulation system, and/or otherwise arranged relative to any other system. In these variants, the manipulation system can physically contact (e.g., touch, nudge, push, etc.) and/or generate fluid motion (e.g., via manipulation system motion, via injecting and/or aspirating fluid, etc.) near: the gamete, cell container, and/or other component to be positioned. In a first variant, the positioning system includes the manipulation system and/or interfaces directly with the manipulation system. For example, the positioning system can include actuators moving: an aspirator, needle, and/or micropipette of the manipulation system. In a second variant, the positioning system is separate and/or distinct from the manipulation system (e.g., the positioning system includes an actuated platform separate from the manipulation system components). In a third variant, the positioning system includes a first system separate from the manipulation system and a second system connected to and/or a part of the manipulation system. For example, the positioning system includes manipulation system actuation as well as a separate actuated platform (e.g., actuation of a manipulation system needle/aspirator for reorienting the gamete and a separate actuated platform x, y, and/or z actuation).

Figure 11:
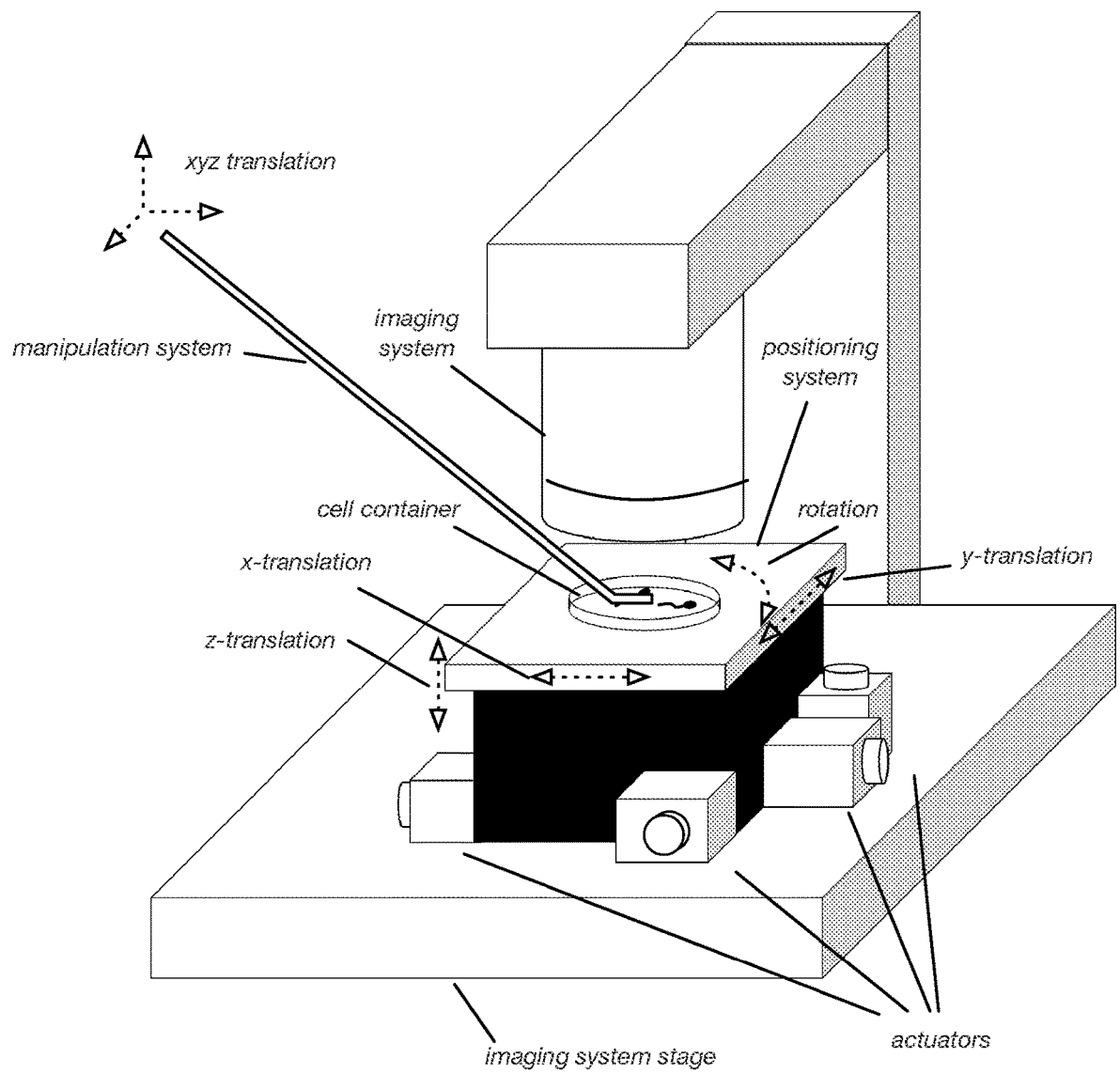
FIG. 11 is an example of the system, including a positioning system.
Figure 12:
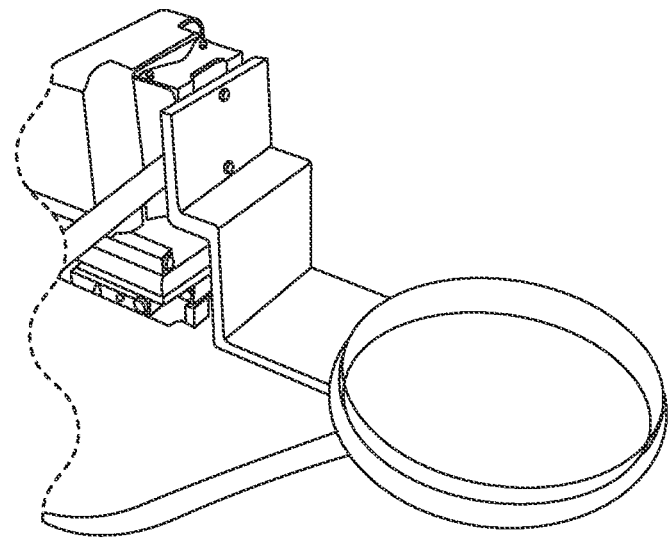
FIG. 12 is an illustrative example of the positioning system.
Figure 12:
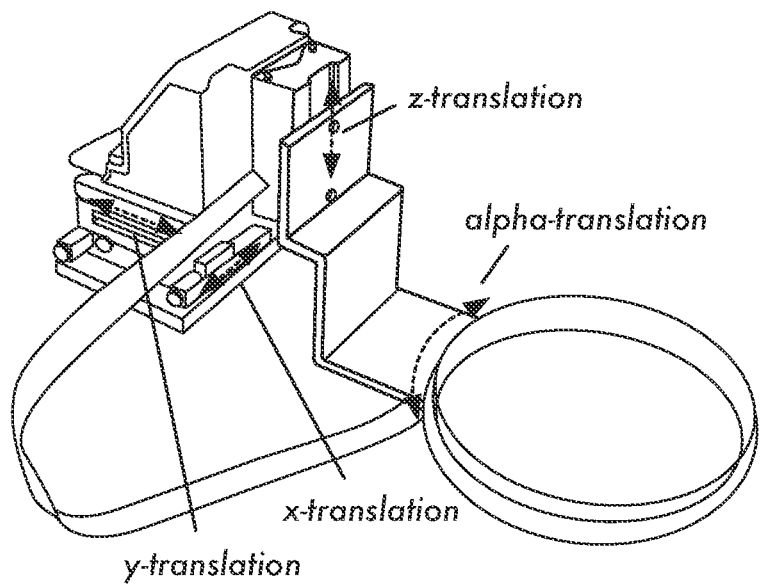

Examples of the positioning system are shown in FIG. 11 and FIG. 12.

However, the positioning system can be otherwise configured.

Figure 18:
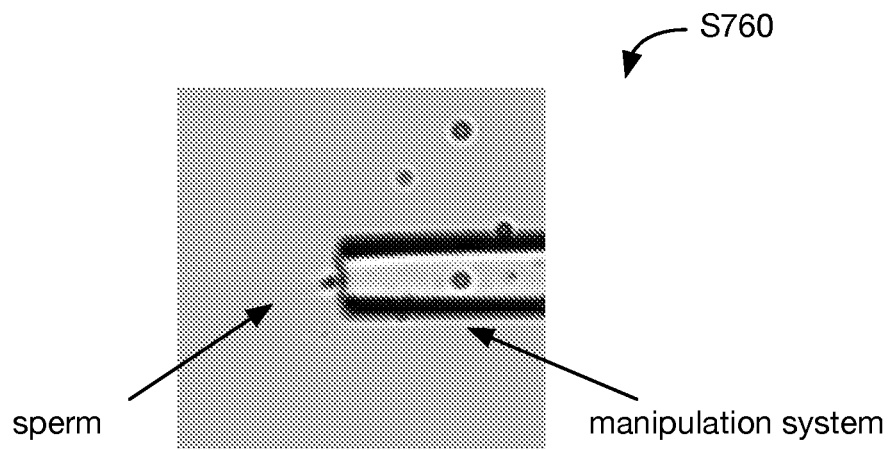
FIG. 18 depicts an illustrative example of retrieving a gamete.

The manipulation system can function to facilitate physically isolating a gamete, immobilizing a gamete, reorienting a gamete, retrieving a gamete, and/or otherwise manipulating one or more gametes for downstream use (e.g., to acquire measurements of the gamete, for attribute value determination, gamete transfer, assistive reproductive technologies (ART) processes, etc.). The manipulation system can include one or more systems. In a first example, the manipulation system includes a single system that can optionally perform multiple manipulation functions (e.g., isolation, immobilization, retrieval, etc.). In a second example, the manipulation system can include: an immobilization system (e.g., an intracytoplasmic sperm injection (ICSI) or intracytoplasmic morphologically selected sperm injection (IMSI) needle and/or micropipette, a blade, an aspirator, a laser, suction end effector, nozzle, etc.), a retrieval system (e.g., an ICSI or IMSI needle and/or micropipette, an aspirator, suction end effector, nozzle, etc.), an isolation system (e.g., microfluidic cell sorter, a microfluidic chip, any cell sorting devices, optical tweezers, needle, micropipette, aspirator, etc.), and/or any other gamete manipulation system. An aspirator can be a standard micromanipulation needle (e.g., micropipette), a micromanipulation needle with a larger than standard bore (e.g., a needle with a 17-18 micrometer bore, to minimize damage to the gamete), an ICSI or IMSI needle and/or micropipette, and/or any other suitable needle, micropipette, and/or aspirator. An example is shown in FIG. 18. In a specific example, the aspirator includes a bend such that a first section (e.g., the tip) of the aspirator is substantially parallel to the base of the cell container (e.g., wherein the first section can be used for immobilization) and a second section is not parallel to the base of the cell container (e.g., to not interfere with a lip of the cell container). The aspirator can optionally be connected to a piston (e.g., directly attached, connected via a tube, and/or otherwise connected), wherein the piston can inhale and/or exhale (e.g., applying positive and/or negative aspiration force). The piston can be hydraulic (e.g., filled with oil and/or any other fluid), pneumatic (e.g., filled with air), and/or otherwise configured. The piston can optionally be driven using a linear actuator (e.g., digital linear actuator), a rotary motor (e.g., a lead screw), and/or any other actuation system.

The manipulation system and/or one or more components therein can be actuated in 1D, 2D, 3D, 4D, 5D, 6D, and/or any number of dimensions. In specific examples, the manipulation system can include an actuation stage (e.g., linear stage, xy stage, xyz stage, xyzr stage, etc.), robotic arm (e.g., delta stage, Stewart platform, linear link, spherical parallel manipulator, etc.), a combination thereof, and/or any other actuation system. The manipulation system and/or one or more components therein can be automatically actuated, manually actuated, and/or stationary. The manipulation system actuation can be based on: actuation instructions, a user (e.g., manual inputs from a user), and/or any otherwise determined. The manipulation system is preferably actuatable (e.g., x/y/z actuation, rotation, etc.) relative to the positioning system (e.g., the imaging system stage, an actuated platform mounted to the imaging system stage, etc.), but can alternatively be stationary and/or not actuatable relative to the positioning system. In a first example, the manipulation system is actuated in fewer dimensions (e.g., no actuation, only z-direction, only x/y directions, x/y/z directions without rotation, etc.) than the positioning system (e.g., x/y directions; x/y/z directions; x/y/z directions and rotation, etc.). In a second example, the manipulation system is actuated in the same number of dimensions as the positioning system. In a third example, the manipulation system is actuated in a greater number of dimensions (e.g., x/y/z directions, 6D robotic arm, etc.) than the positioning system (e.g., x/y directions, x/y/z directions, etc.). However, actuation axes for one or more components can be otherwise divided across the imaging system, positioning system, and/or the manipulation system.

The manipulation system can optionally be connected to the imaging system (e.g., mounted on the microscope stage; a laser connected to the objective lens; etc.), connected to and/or a part of the positioning system (e.g., actuated by the positioning system), located on a separate platform, mounted on a robotic arm, and/or otherwise configured relative to the imaging system, the positioning system and/or any other system or module. In these variants, the manipulation system is preferably statically connected to the other component; alternatively, the manipulation system can be actuatably connected to the other component.

However, the manipulation system can be otherwise configured.

The selection system can function to analyze gametes (e.g., determine attribute values for a gamete) and/or select a gamete from a set (e.g., based on the attribute values). The gamete(s) can be selected for: repositioning, manipulation, use in ART (e.g., fertilization), and/or any other purpose.

The selection system can include one or more models (e.g., gamete attribute models, selection models, etc.), a computing system, one or more specialists (e.g., embryologists, reproductive endocrinologists, andrologists, etc.), and/or any other suitable system or module. The gamete attribute models and/or selection models are preferably biased toward resulting in little or no false positive gamete selections (e.g., where a nonviable gamete is selected), but can be biased to have little or no false negative gamete selections, or be otherwise trained. The selection system can be local (e.g., collocated in the same facility) and/or remote (e.g., be a cloud-based system) to the imaging system, the manipulation system, positioning system, and/or any other system component. In an illustrative example, a video can be sampled at the imaging system and then transmitted to the selection system. The selection system can then identify a gamete for selection and transmit the selection to the positioning system to move the gamete and/or to the manipulation system to manipulate the gamete. However, the selection system can be otherwise configured.

Models in the system (e.g., gamete detection model, tracking model, motion model, appearance model, feature extraction model, gamete attribute model, selection model, focus model, etc.) can leverage classical or traditional approaches (e.g., models with manually coded parameters; models using manually-selected feature descriptors, such as SIFT, SURF, FAST, Hough transforms, geometric hashing, etc. paired with an SVN, k-nearest neighbors, and/or other classifiers; models that are entirely or partially manually defined; etc.), leverage machine learning approaches (e.g., have learned parameters), and/or be otherwise constructed. Each model can use one or more of: regression, classification (e.g., a multiclass classifier, a binary classifier, etc.), clustering, neural networks (e.g., CNNs, DNNs, RNN, LSTM, etc.), rules, heuristics, equations (e.g., weighted equations, etc.), instance-based methods (e.g., nearest neighbor), object detection methods, segmentation methods, regularization methods (e.g., ridge regression), decision trees, random forest, Bayesian methods (e.g., Naïve Bayes, Markov), kernel methods, probability, deterministics, genetic programs, generative models, support vectors, and/or any other suitable method. The models can be learned (e.g., using supervised learning, self supervised learning, unsupervised learning, transfer learning, etc.), fit, trained, predetermined, and/or can be otherwise determined. Models can be trained to predict specialist labels using data from a specialist set (e.g., labeled gametes; labeled gamete videos, sub-videos, and/or images; etc.), trained to predict any other labels (e.g., focus labels, orientation labels, etc.), trained or programmed to calculate a quantitative and/or qualitative attribute value, and/or otherwise generated. In an example, the specialist labels can be: attribute values (e.g., based on a World Health Organization gamete classification system), gamete bounding boxes, selected gametes, and/or any other label. Models can be trained once, iteratively trained (e.g., as more training data is generated by the method), and/or trained or retrained any number of times.

The computing system can include one or more: CPUs, GPUs, custom FPGA/ASICS, microprocessors, servers, cloud computing, and/or any other suitable components. The computing system can be local, remote, distributed, or otherwise arranged relative to the imaging system and/or any other system or module. However, the computing system can be otherwise configured.

However, the system can include any other suitable components.

5. Method

As shown in FIG. 1, the method can include: sampling a video of a scene having a gamete S100; tracking the gamete S200; and positioning the gamete within a target region S500. The method can optionally include: determining attribute values for the gamete S300; selecting the gamete S400; reorienting the gamete S600; manipulating the gamete S700; and/or any other suitable steps.

All or portions of the method can be performed in real time (e.g., responsive to a request), iteratively, at each frame of a sampled video S100, at each timestep of an actuator (e.g., positioning system actuator) or a multiple thereof, asynchronously, periodically, concurrently and/or contemporaneously, and/or at any other suitable time. All or a portion of the method can be performed automatically, manually, semi-automatically, and/or otherwise performed. All or portions of the method can be performed by one or more components of the system, by a user, and/or by any other suitable system.

All or portions of the method can be performed for a single gamete (e.g., individually isolated using a microfluidic isolation system, a single gamete in a set of gametes, etc.) and/or for a set of gametes (e.g., a plurality of gametes, from one or more gamete samples from the same or different patient). All or portions of the method can be performed once for each gamete, iteratively for each gamete in the set, once for the gamete set, iteratively for each gamete set, and/or performed any other number of times. Different instances of the method can be concurrently or contemporaneously performed for different gametes in the same (or different) sample; additionally or alternatively, different method instances for different gametes can be performed asynchronously (e.g., sequentially, serially, etc.).

The set of gametes can be selected from a population of gametes in a sample, include all gametes in an image and/or field of view, include all gametes in a sample, include all gametes in a scene, be a subset thereof, and/or be otherwise defined. The gametes can be mobile or static. Examples of the gametes include: spermatozoa, ovum, and/or other gametes. The gametes can be: human gametes, animal gametes (e.g., mouse, bovine, porcine, fowl, etc.), and/or from other animals.

In examples, portions of the method can be performed as disclosed in U.S. application Ser. No. 17/871,665 filed 22 Jul. 2022, which is incorporated herein in its entirety by this reference. However, portions of the method can be otherwise determined.

Sampling a video of a scene having a gamete S100 functions to obtain sensor measurements of one or more gametes. S100 is preferably performed by the imaging system, but can be performed by another system. S100 can be performed continuously, periodically, iteratively (e.g., for a set of gametes, for a set of time periods, iteratively with S500 and/or S600, etc.), in response to a trigger, and/or at any other frequency. S100 can be performed before one or more of S200-S700 (e.g., wherein the video is used in S200-S700), after selecting a gamete S400 (e.g., where the video is sampled for one or more selected gametes), during one or more of S200-S700, and/or at any other suitable time.

The gamete can be isolated (e.g., via S700, using the manipulation system) and/or not isolated from a population of gametes. The gamete can be in a prepared sample (e.g., to slow gamete motility, to dilute gamete concentration, etc.), an unprepared sample, and/or other sample. In a first variant, the sample can be prepared using a motility retardant, such as: polyvinylpyrrolidone (PVP), hyaluronate-containing products, mucus substitutes, viscous liquids, and/or other motility retardants. In a second variant, the sample can include seminal fluid (e.g., diluted and/or undiluted). The seminal fluid is preferably from the same donor as the sample gametes, but alternatively can be from one or more different donors. In a third variant, the sample can be prepared using a culture media. In a fourth variant, the sample can be unprepared. However, the sample can be otherwise prepared.

The scene (e.g., slide, petri dish, tray, well, vial, cell container, workspace, etc.) is preferably configured such that the gametes lie in a single layer, but can alternatively be sized such that gametes overlap each other.

S100 preferably includes sampling a timeseries of images (e.g., video, sub-video, series of video frames, etc.), but can additionally or alternatively include sampling a single image (e.g., still image), sampling depth or height information (e.g., by focusing on different focal planes, by changing the slide height, by using a depth sensor, etc.), and/or other images.

The image (e.g., still image or video frame) can be a 2D image (e.g., RGB image, multispectral image, hyperspectral image, etc.), a 3D image (e.g., stereoimage, time of flight image, projected light image, depth measurement, point cloud, etc.). The image can be: a sub-image associated with a subregion of the overall scene, an image that encompasses the entire scene, an image that encompasses a majority of the scene, and/or an image that encompasses any other suitable portion of the scene. When the image is a sub-image, the sub-image can be: cropped from a full-frame image; sampled (e.g., contemporaneously, concurrently, asynchronously) with other sub-images (e.g., by the same or different imaging systems), but can be otherwise determined. However, the video can be otherwise determined.

Tracking the gamete S200 functions to identify the same gamete instance across images, such that gamete features and/or attribute values extracted from different images can be associated with the same gamete. S200 can optionally be used to determine gamete-associated image segments (e.g., sub-video frames). S200 is preferably performed by the tracking system, but can be performed by another system. S200 can be performed after S100, after S400 (e.g., for the selected gamete), during one or more of S500-S700, iteratively with S500 and/or S600 (e.g., iteratively tracking and repositioning, iteratively tracking and reorienting, etc.), during and/or after all or parts of S700 (e.g., tracking during and/or after gamete immobilization, gamete retrieval, and/or any other gamete manipulation), and/or at any other time.

S200 can be performed for: one gamete at a time, multiple gametes at a time, and/or any other number of gametes.

The tracked gamete can be: all visible gametes (e.g., within the imaging system's field of view), a randomly-selected gamete, one or more gametes selected using a set of criteria (e.g., motion above a threshold level, motion having a target pattern, morphology having a certain set of features, size above a threshold size, etc.), one or more gametes selected in S400, and/or any other gamete.

The gamete can be digitally tracked (e.g., tracked across sequential images, with or without moving the imaging system relative to the physical scene), physically tracked (e.g., via S500), and/or otherwise tracked.

S200 can be performed per image (e.g., on the full image of each image, a mosaiced super-image of the scene generated from different sub-images, a subportion of the image, etc.), on the video (e.g., a series of images, the video from S100, a sub-video, etc.), and/or for any other set of images. S200 can be performed using the 2D image, 3D data, and/or any other data. The gamete can be tracked across consecutive images, nonconsecutive images, and/or any set of images. The gamete can be tracked: within a scene subregion (e.g., coextensive with the imaging system's field of view; within a subregion of the field of view depicting the manipulation system, such as a subregion depicting all or parts of an aspirator; etc.), only within the scene subregion depicted within the imaging system's field of view, across all or a portion of the scene, and/or across any other physical region. The gamete is preferably tracked using gamete features (e.g., appearance features, motion features, location, etc.), but can be tracked based on the images (e.g., sliding window of video frames, all images, image segments, etc.), a predicted gamete location, and/or any other suitable information. As used herein, features preferably refer to low-level features extracted from the raw data (e.g., computer vision features, such as edges, blobs, corners, gradients, etc.; timeseries features, such as amplitude, frequency, energy, etc.), but can additionally or alternatively refer to attributes and/or other information extractable from the raw data. The features can be extracted by autoencoders, (e.g., variational, denoising, convolutional, sparse, etc.), t-distributed stochastic neighbor embedding (t-SNE), uniform manifold approximation and projection (UMAP), locally linear embedding (LLE), linear discriminant analysis (LDA), independent component analysis (ICA), principal component analysis (PCA), and/or any other suitable feature extraction model.

The gamete can be tracked using: object detection methods (e.g., using a trained gamete detector, using a shape-fitting model, etc.), object tracking and localization models, optical flow (e.g., phase correlation; block-based methods; differential methods, such as Lucas-Kanade, Horn-Schnuck, Buxton-Buxton, Black-Jepson, and/or variational methods; discrete optimization methods; etc.), other tracking modules (e.g., gamete trackers), and/or any other tracking method. The gamete can be tracked using: traditional computer vision methods (e.g., with hand-selected features, hand-coded relationships, etc.), deep learning methods (e.g., with learned features, learned weights, etc.), and/or any other method or model. The gamete tracking models can be trained using: specialist-labelled images (e.g., that label image regions as depicting gametes); and/or otherwise trained. Over the course of the video, S200 can output: a track or tracklet for the gamete (e.g., timeseries of locations, positions, bounding box positions, or occupied pixels); kinematics; and/or other information. The track can subsequently be used to generate gamete sub-videos, determine motility attribute values, and/or otherwise used. The track can be 2D (e.g., 2D positions over time); 3D (e.g., 3D positions over time); and/or have any other suitable set of dimensions. The track can be generated from: the video, a sub-video, a series of sub-videos, a sliding window of video frames, all video frames, a single image, and/or from any other data. Each track can be associated with a gamete identifier (e.g., for the tracked gamete).

The gamete tracking models can track the gamete across images (e.g., cross-correlated across images) based on: appearance (e.g., based on appearance encoding distance or similarity, based on morphology attribute values determined based on appearance features, etc.), motion (e.g., actual vs predicted, similar motion vectors, etc.), a combination thereof, and/or other information. In a first embodiment, the gamete can be identified (e.g., matched) based on motion features without using appearance features (e.g., using only motion features). In a second embodiment, the gamete can be identified based on appearance features without using motion features (e.g., using only appearance features). In an illustrative example, gametes are matched across frames when the head morphology of the gametes match (e.g., shape, attribute values, and/or other morphology parameter match within a threshold). In a third embodiment, the gamete can be identified based on a combination of appearance and motion features. This can increase the identification accuracy because gametes are asymmetric and rotate about a longitudinal axis during translation (e.g., successive images of the same gamete may look different). In a first example, gametes can be matched across frames based on appearance first, where predicted location is used as a tiebreaker. In a second example, the gametes can be matched based on location first (e.g., to identify candidate gametes or image segments), wherein appearance-based matching is localized to the predicted gamete location. In a third example, appearance and predicted location-based matching are performed independently, wherein a gamete is considered a match if both methods agree. However, the gametes can be otherwise tracked.

When the image is a sub-image (e.g., of a subregion of the scene), the method can additionally include combining the appearance encoding and/or predicted gamete locations across all sub-images, such that the gamete is tracked across the entire scene. Alternatively, the gamete can be tracked within sub-images only, wherein gametes that cross subregion boundaries are ignored.

However, a track for a gamete can be otherwise determined.

The method can optionally include determining a sub-video depicting the gamete, which can function to generate a set of sub-images, specific to the gamete, for downstream use (e.g., to provide to the specialist set, to determine attribute values, etc.). By limiting the visual input to the region surrounding the gamete (e.g., including only the gamete or including a limited set of adjacent gametes), using a sub-video can decrease the model input noise, which, in turn, can result in more accurate model outputs. The sub-video can be determined in real-time with S100, asynchronously with S100, after S200 (e.g., immediately after, asynchronously, etc.), and/or at any other time. Each sub-video can depict a single gamete (e.g., the tracked gamete in S200; excluding other gametes; etc.), multiple gametes (e.g., the tracked gamete and adjacent gametes), and/or any other set of gametes.

The sub-video is preferably determined based on the video sampled in S100, but can alternatively be independently sampled (e.g., sampled based on the track determined in S200). The sub-video can include: a subset of each image (e.g., cropped images, image segments, sub-images, etc.), a subset of the image timeseries (e.g., spanning a limited time period, be a video clip, etc.), and/or otherwise defined relative to the video. The sub-video can be constructed such that the gamete is centered in the sub-video (e.g., wherein the sub-video field of view dynamically follows the gamete), constructed such that the gamete is always visible or depicted, but not necessarily centered in the sub-video, and/or otherwise constructed.

The sub-video is preferably determined based on the gamete track (e.g., S200), but can alternatively be otherwise determined. In a first variant, the video images are segmented into gamete image segments after gamete identification. The image segments are then assigned a common gamete identifier after gamete matching and aggregated into a timeseries to generate the sub-video. In a second variant, image segments of the gamete are extracted from each image based on the gamete position for each image timestep. In a third variant, a bounding box or other indicator that tracks the gamete through the frame can be rendered over the images of the sub-video (e.g., wherein the sub-video can include full frame images and/or cropped images).

However, the sub-video can be otherwise determined.

The method can optionally include determining attribute values for the gamete S300, which can function to calculate, predict, and/or otherwise determine gamete information used to: facilitate gamete repositioning, reorientation, and/or any other manipulation; evaluate gamete quality and/or compare gametes against each other; and/or otherwise used. S300 can be performed after S100 and/or S200; before S600 (e.g., an orientation attribute value used in gamete reorientation); before S700 (e.g., a gamete tail attribute value used in gamete manipulation); at a predetermined frequency (e.g., each image, every N images, etc.); after a threshold condition is met (e.g., after a sub-video is generated, after a predetermined number of images have been captured, after a confidence score exceeds a threshold, etc.); iteratively (e.g., until a stop condition is met); and/or at any other suitable time. S300 can optionally be performed in real- or near-real time relative to sampling the video (S100) and/or tracking the gamete (S200).

Each gamete can be associated with a set of attribute values. The set of attribute values can include: different values for the same attribute (e.g., a timeseries of values for an attribute, etc.); values for different attributes; different values for different attributes; and/or any other suitable attribute values.

The gamete attribute values can be: predicted, calculated, or otherwise determined. Examples of attribute values include: a rating or score (e.g., quantitative, relative, qualitative, etc.), a ranking, a classification, a label (e.g., specialist label), a degree of healthiness and/or normality (e.g., relative to a reference gamete population), a probability (e.g., probability of selection by a specialist, probability of successful post-fertilization development, etc.), morphology attribute value (e.g., gamete tail attribute value), motility attribute value, orientation attribute value, gamete measurement (e.g., destructive information values, DFI, PGT, vitality, etc.), post-fertilization development data, and/or values for any other attribute. Attribute values can be: qualitative, quantitative, relative, discrete, continuous, a classification, numeric, binary, and/or be otherwise characterized.

Gamete attribute values can be determined based on a set of inputs, including one or more of: the video, one or more sub-videos, gamete features (e.g., motion features and/or appearance features extracted using a feature extraction model based on a video and/or sub-video), a gamete track (e.g., from S200), feature descriptors extracted from the video and/or sub-videos (e.g., nonsemantic and/or semantic features), attribute values for the gamete from prior evaluation periods, attribute values for other gametes (e.g., in the sample), a combination thereof, and/or any other suitable noninvasive or nondestructive inputs, and/or exclude any of the above (e.g., excluding semantic features extracted from the video, sub-video, and/or images). However, any other input can be used.

The inputs can optionally be filtered, weighted, selected, downsampled, upsampled, limited to a predetermined length or time window, limited to a predetermined number of datapoints, and/or otherwise preprocessed. However, the inputs can alternatively be unprocessed.

In one embodiment, image inputs can be weighted and/or selected based on the gamete roll orientation (e.g., the orientation of the gamete around a roll or longitudinal axis) and/or whether a frame depicts the gamete's flat face. In an illustrative example, a first frame depicting the gamete where the flat side of the gamete is 95% visible in the image can be weighted higher than a second frame depicting the gamete where the flat side is 20% visible in the image. In a first example, image selection and/or weighting can be performed using an attention model, wherein inputs (e.g., features extracted from each frame) are weighted based on an attention score (e.g., for the frame) determined using the attention model. The attention score for a frame can be positively correlated with the frame depicting the flat side of the gamete (e.g., the flat side is parallel to the camera, parallel to the scene, etc.). The attention model can be part of the gamete attribute model (e.g., where the gamete attribute model uses attention layers, where the gamete attribute model includes an attention mechanism, etc.) or alternatively separate from the gamete attribute model (e.g., where the attention model pre-selects and/or pre-weights the images). In variants, the attention model, layers, and/or mechanism can be trained (e.g., explicitly or as part of an end-to-end model) to focus or upweight images depicting a flat side of the gamete, images depicting gametes, and/or any other subject. In a second example, the roll orientation of the gamete can be determined by calculating the surface area of the gamete visible in the image, where the image is selected when the surface area exceeds a threshold. In a third example, the roll orientation of the gamete can be determined by fitting a geometric shape (e.g., ellipse, polygon, etc.) to the gamete head, where the image is selected when the fit is above a threshold percentage. In a fourth example, the roll orientation of the gamete can be determined by using a 3D model of the gamete (e.g., generated based on the video and/or the gamete track), where the image is selected when more than a threshold proportion of the flat face (e.g., identified on the 3D model) is depicted in the image. However, the gamete roll orientation can be otherwise determined, and/or the gamete images can be otherwise selected or weighted.

Gamete attribute values can be: manually determined, determined using one or more gamete attribute models (e.g., multiple models each trained to determine an attribute value for the respective attribute; an ensemble of models; etc.), determined using explainability methods, determined experimentally, and/or otherwise determined. The gamete attribute model can be a classical model or traditional model and/or can be a deep learning model.

In a first variant, the gamete attribute models are classical or traditional models, wherein the features can be manually selected, the parameters can be manually encoded, the feature transforms can be manually defined, and/or any other suitable portion of the model can be manually specified. For example, the attribute values can be determined using an equation, lookup table, scoring engine, kinematic model, dynamic model, geometric model, object detectors, segmentation methods, heuristics, computer-aided sperm analysis (CASA) methods, computer-aided sperm morphometric assessment (CASMA) methods, and/or any other method. In this embodiment, the attribute values are preferably determined based on semantic features (e.g., geometric measurements, motion measurements, etc.) extracted from one or more images, but can alternatively be determined based on non-semantic features.

A first embodiment includes extracting motion attribute values for the gamete. The motion attributes can include:

gamete kinematics (e.g., velocity, acceleration, etc.), heading, summary features (e.g., average path or velocity, curvilinear path or velocity, straight-line path or velocity, amplitude of lateral head displacement, linearity, wobble, straightness, beat-cross frequency, mean angular displacement, etc.), and/or other features. The kinematics can be linear, rotational, and/or motion in other degrees of freedom. Illustrative examples of calculated motility attribute values include: curvilinear velocity (e.g., time-averaged velocity of a gamete head along its curvilinear path), straight-line velocity (e.g., time-averaged velocity of a gamete head along the straight line between a first and second detected positions), average path velocity (e.g., time-averaged velocity of a gamete head along its average path), amplitude of lateral head displacement (e.g., magnitude of lateral displacement of a gamete head), linearity, wobble (e.g., measure of oscillation of the actual path about the average path), beat-cross frequency (e.g., the average rate at which the curvilinear path crosses the average path), mean angular displacement (e.g., the time-averaged absolute values of the instantaneous turning angle of the sperm head along its curvilinear trajectory), similarity to a helix, CASA variables, and/or any other calculated mobility attribute value. In a specific example, a gamete orientation attribute value can be determined based on a motion attribute value (e.g., the orientation is the direction of gamete movement). Motility attribute values are preferably determined using temporally adjacent images (e.g., images from two or more timesteps), but can alternatively be performed using a single image and motion features from a prior timestep or using other input. The motion features can be extracted using: a physics model, motion model, motion estimators, optical flow (e.g., for higher gamete concentrations or scenes with more visual features), filtering and data association (e.g., Kalman filter, particle filter), target representation and localization (e.g., kernel-based tracking, contour tracking), a trained DNN, calculated using an equation, and/or other motion modules.

A second embodiment includes estimating a predicted location for the gamete. The predicted location is preferably the predicted gamete location within the next image (e.g., for timestep t+1), but can alternatively be the gamete location (e.g., within the image or within the scene) N images into the future and/or the past. This embodiment can be performed using the current location, the gamete's motion features, the entire image, an image segment, and/or other input. The predicted gamete location can be estimated using a motion model, a filter (e.g., Kalman filter, Particle filter), be calculated, be looked up, and/or be otherwise determined.

A third embodiment includes determining an attribute value (e.g., a morphology attribute value, a gamete tail attribute value, an orientation attribute value, a current gamete location, etc.) based on a set of gamete appearance features (e.g., geometric dimensions, appearance encoding, etc.) extracted from one or more images. The gamete appearance features can include: gradients, edges, corners, blobs, boundaries, and/or any other visual feature. The gamete appearance features are preferably nonsemantic, but can alternatively be semantic. The appearance features can be extracted using: segmentation methods (e.g., instance-based segmentation, semantic segmentation, etc.), object detection methods (e.g., Viola-Jones, SIFT, HOG, region proposals, SSD, YOLO, deep learning models, etc.), image segmentation methods (e.g., motion based segmentation, thresholding, etc.), heuristics (e.g., combination of object detectors and heuristics), filters (e.g., histogram filters), classical and/or deep learning models, and/or other methods. In this embodiment, features used to calculate the attribute value can be manually selected (e.g., the head boundary is used to determine the head shape score or classification, the tail boundary is used to determine the tail angle, etc.), selected based on a set of rules or heuristics, and/or otherwise selected. The attribute value can be: classified, calculated, and/or otherwise determined based on the appearance feature values.

In a specific example, a mask of all or parts of the gamete (e.g., the head, neck, tail, part of the tail, any gamete component, etc.) can be generated based on the appearance features (e.g., extracted using a trained object detector and/or a set of heuristics), wherein the mask is used to determine one or more attribute values. Masks can be generated using deep learning methods (e.g., UNET), traditional computer vision techniques, and/or any other suitable methods. In an illustrative example, one or more pixels in each frame of the video can be identified that correspond to the gamete or a component of the gamete (e.g., the gamete tail). The mask can optionally be an aggregated mask (e.g., temporal aggregation, aggregating mask segments, weighted average of mask pixels based on probability a pixel corresponds to the tail, etc.). Temporal aggregation (e.g., temporal averaging) can be performed across frames of the video within a time window, wherein the time window can be between 0s-5s or any range or value therebetween (e.g., 0.05s, 0.1s, 0.2s, 0.3s, 0.4s, 0.5s, 1s, 2s, etc.), but can alternatively be greater than 5s. Temporal aggregation can optionally function to filter out spurious masks (e.g., due to debris, bubbles, other gametes passing, etc.). In a specific example of temporal aggregation, an intermediate mask is generated for each video frame within the time window, wherein the intermediate masks are aggregated (e.g., using averaging, weighted averaging, etc.) to generate an overall mask.

Illustrative examples of calculated morphology attribute values include: head and mid-piece dimensions (e.g., length of major and minor axes), head ellipticity and regularity, neck angle, vacuole parameters (e.g., number, density, area per vacuole, overall area, vacuole ratio relative to head), stain-dependent measurement of the acrosome area, CASMA variables, and/or any other calculated morphology attribute value. Illustrative examples of calculated gamete tail attribute values include: a gamete tail representation (e.g., a set of pixels and/or coordinates corresponding to all or parts of the tail, a function fit to all or parts of the tail, a mask of all or parts of the tail, etc.), a location associated with the tail (e.g., tail center, a location on the gamete tail), an angle (e.g., direction) of all or a portion of the tail, tail length, tail width, tail curvature (e.g., coiling), a tail primary axis, and/or any other attribute value. Illustrative examples of calculated gamete orientation attribute values include: any gamete tail attribute value (e.g., tail angle, tail primary axis, etc.); an axis of a representation of all or a portion of the tail (e.g., based on a gamete tail attribute value); an orientation classification; and/or any other attribute value. Illustrative examples of the calculated gamete location (e.g., current position) can include: coordinates of the gamete head (e.g., a centroid of the head), the center of the overall gamete, the tail tip (e.g., determined based on a representation of the tail), and/or any other location. The gamete location and/or the orientation (e.g., a gamete pose) can be defined relative to a static and/or dynamic reference frame (e.g., reference frame associated with: the video scene, the field of view, a target region and/or target orientation, a manipulation region, the imaging system, the positioning system, the cell container, one or more principal axes of the gamete, a reference image, the manipulation system position, etc.). In examples, the gamete location and/or orientation is determined based on the pixel indices of the gamete's pixels within the image and the scene coordinates associated with said pixel indices, based on a distance to a known scene reference, and/or otherwise determined relative to a reference.

Figure 16:
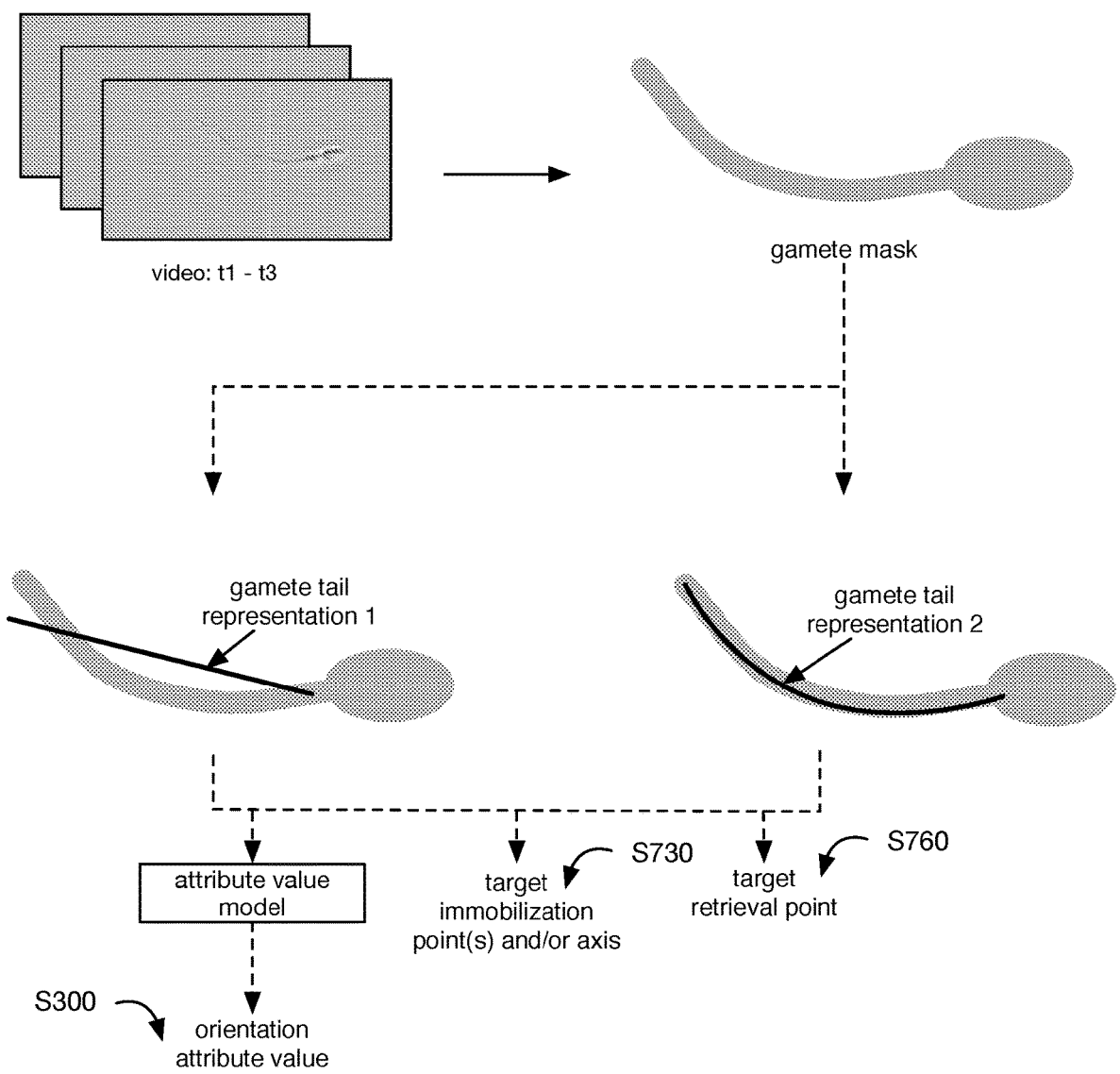
FIG. 16 depicts an illustrative example of a gamete tail representation.

In a first example, determining the orientation attribute value includes determining a mask of all or parts of the gamete (e.g., gamete neck mask, gamete tail mask, gamete head mask, without a full mask of the gamete tail, etc.) and determining a tail primary axis based on the mask. In specific examples, the tail primary axis can be determined by averaging the lateral extrema of the tail mask points, by using a principal component analysis model (e.g., applied to the tail mask), and/or otherwise determining a tail axis. In a second example, determining the orientation attribute value includes determining a gamete tail representation and determining the orientation attribute value based on the gamete tail representation (e.g., an axis of the gamete tail representation; the gamete tail pose relative to the gamete head; etc.). The gamete tail representation can optionally be a function (e.g., nonlinear, linear, polynomial, piecewise function, exponential, power, periodic, spline, skeletonization, any regression, etc.) determined based on: all or parts of a gamete tail mask (e.g., one or more pixels corresponding to the tail, a probability that a pixel corresponds to the tail, etc.), known or estimated tail parameters (e.g., length of tail, approximate length of gamete tails, likely bend direction and/or angle based on an immobilization swipe, etc.), any gamete tail attribute value, and/or any other input. In a first specific example, the function is a linear function fit to the gamete tail mask (e.g., making a straight tail assumption). In a second specific example, the function is a nonlinear function fit to the gamete tail mask (e.g., without making a straight tail assumption). An example is shown in FIG. 16.

In a second variant, gamete attribute models are machine learning (ML) models, wherein feature selection, weighting, relationships, and/or other model aspects can be automatically learned. The machine learning model is preferably the gamete attribute model trained to output a set of gamete attribute values (e.g., a predicted gamete attribute value) based on the inputs. However, the model can be otherwise trained. The ML models can predict, infer, or otherwise determine the respective gamete attribute value(s). The ML models can ingest the video, one or more sub-videos, auxiliary data (e.g., population-level data, attribute values for the gamete from a prior evaluation period, etc.), and/or any other information.

In a first embodiment, a gamete motility attribute value is determined using a gamete attribute model, wherein the gamete attribute model includes one or more trained neural networks (e.g., trained based on specialist-labeled images or tracks). The trained models (such as neural networks) can include motility classifiers (e.g., a multiclass classifier), a cascade of classifiers, regression models (e.g., calculating a motility attribute value for a given motility ontological class), and/or any other suitable model.

In a second embodiment, a gamete morphology attribute value is determined using a gamete attribute model, wherein the gamete attribute model includes one or more trained models (such as neural networks) (e.g., trained based on specialist-labeled images). The trained models can include morphology classifiers (e.g., multiclass classifiers), a cascade of classifiers, regression models (e.g., calculating a morphology attribute value for a given morphology ontological class), and/or any other suitable model.

In a third embodiment, an orientation attribute value is determined using a gamete attribute model, wherein the gamete attribute model includes one or more trained neural networks (e.g., trained based on labeled images or tracks). The trained models (such as neural networks) can include orientation classifiers (e.g., a multiclass classifier), a cascade of classifiers, regression models, object detectors, segmentation methods, and/or any other suitable model.

In a fourth embodiment, a DFI attribute value is determined using a trained gamete attribute model, which can function to predict DFI values without destroying the gamete or rendering the gamete unviable. In this embodiment, the gamete attribute model is preferably trained based on images and/or videos of gametes associated with measured DFI values, but can be otherwise trained. The DFI attribute value is preferably a score, but can alternatively be a class (e.g., representing one or more DFI value ranges), and/or any other suitable DFI characterization.

However, attribute values can be determined using a combination of the above or otherwise determined.

The method can optionally include determining a confidence score for a gamete attribute value, which can be used in gamete selection, model training, and/or other downstream processes. In a first variant, the confidence score can be based on a statistical measure of the distribution of attribute values for the gamete (e.g., standard deviation, variance, interquartile range, etc.). In a second variant, the confidence score can be determined by the gamete attribute model (e.g., be the confidence score associated with the predicted value, etc.). In a third variant, the confidence score can be based on a determined gamete focus level (e.g., gamete image blur). However, the confidence score can be otherwise determined.

Figure 3:
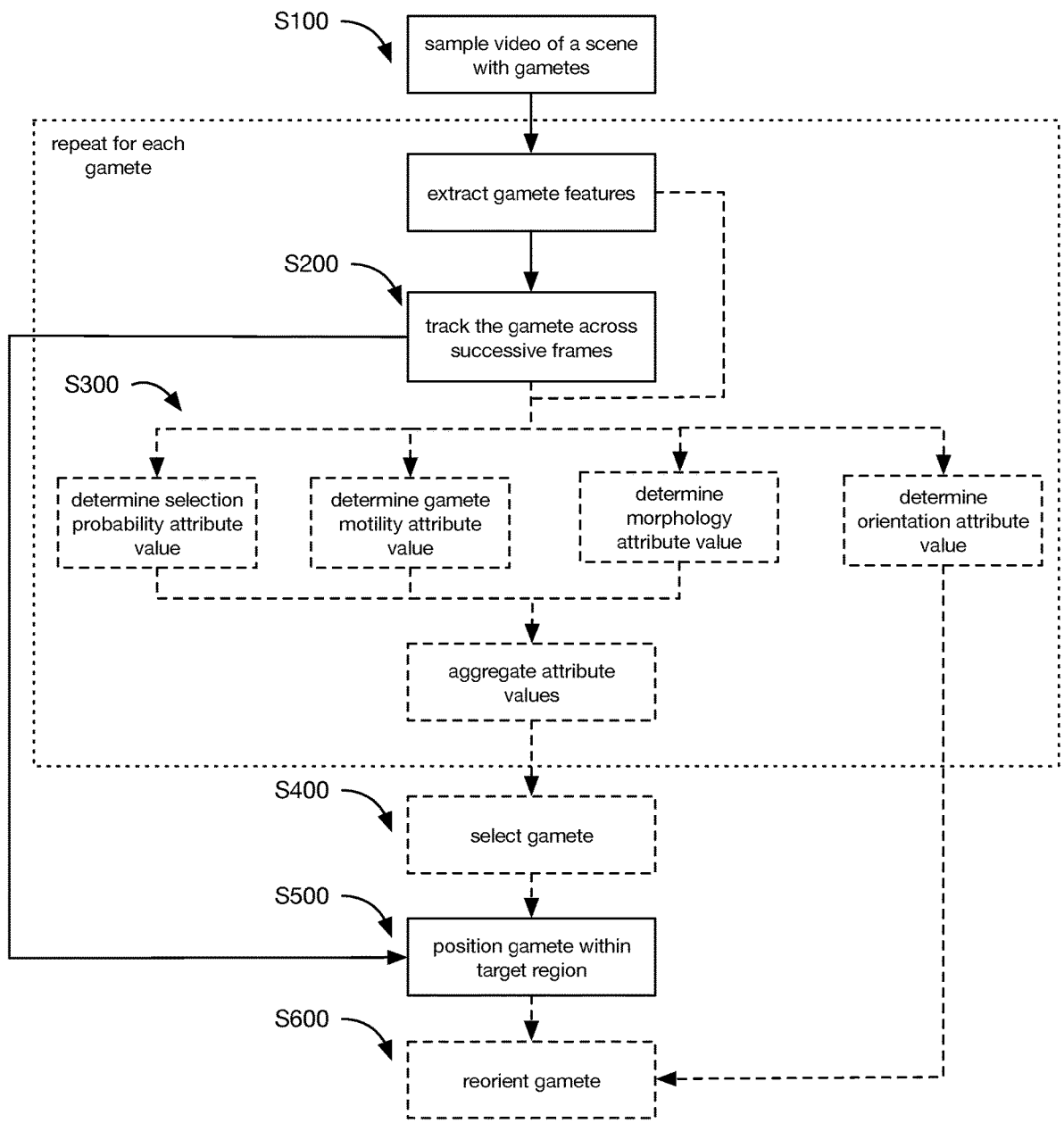
FIG. 3 depicts an example of gamete selection.

The method can optionally include aggregating gamete attribute values, which can function to determine a distribution of gamete attribute values for a given gamete attribute, to determine another gamete attribute value (e.g., a holistic selection metric, a combined attribute value, a summary attribute value, etc.) based on a combination of individual gamete attribute values, determine population-level attribute values, and/or to otherwise process gamete attribute values to improve gamete selection. An example is shown in FIG. 3. The gamete attributes can be aggregated across: images (e.g., wherein the images can be selected and/or weighted), sub-videos, time windows, gametes (e.g., to provide population-level measures which can optionally be used as an input into the selection process), attributes (e.g., calculating a summary metric from values for different gamete attributes for the same gamete), and/or across any other parameter. Aggregation can include: determining a distribution (e.g., wherein the final gamete attribute value can be a statistical measure of the distribution), averaging, weighted averaging, summation, weighted summation, using logical operators, using a set of rules, using voting, and/or any other combination of attribute values. However, attribute values can be otherwise aggregated.

The method can optionally include selecting the gamete S400 which can function to select a gamete from a gamete population (e.g., sample). S400 can identify gametes for: repositioning, manipulation (e.g., physically select the most viable gamete(s) for assistive reproductive processes), model training, attribute value determination, and/or any other gamete use. S400 is preferably performed by the selection system, but can alternatively be performed manually and/or by any other system. S400 can be performed after S100, after S200, after S300, periodically, iteratively, after a threshold condition is met (e.g., after a threshold number of gametes in a sample have been assigned attribute values, after a predetermined number of images have been captured, after a confidence level for a gamete attribute value exceeds a threshold, etc.), until a stop condition is met, and/or at any other suitable time.

Figure 4:
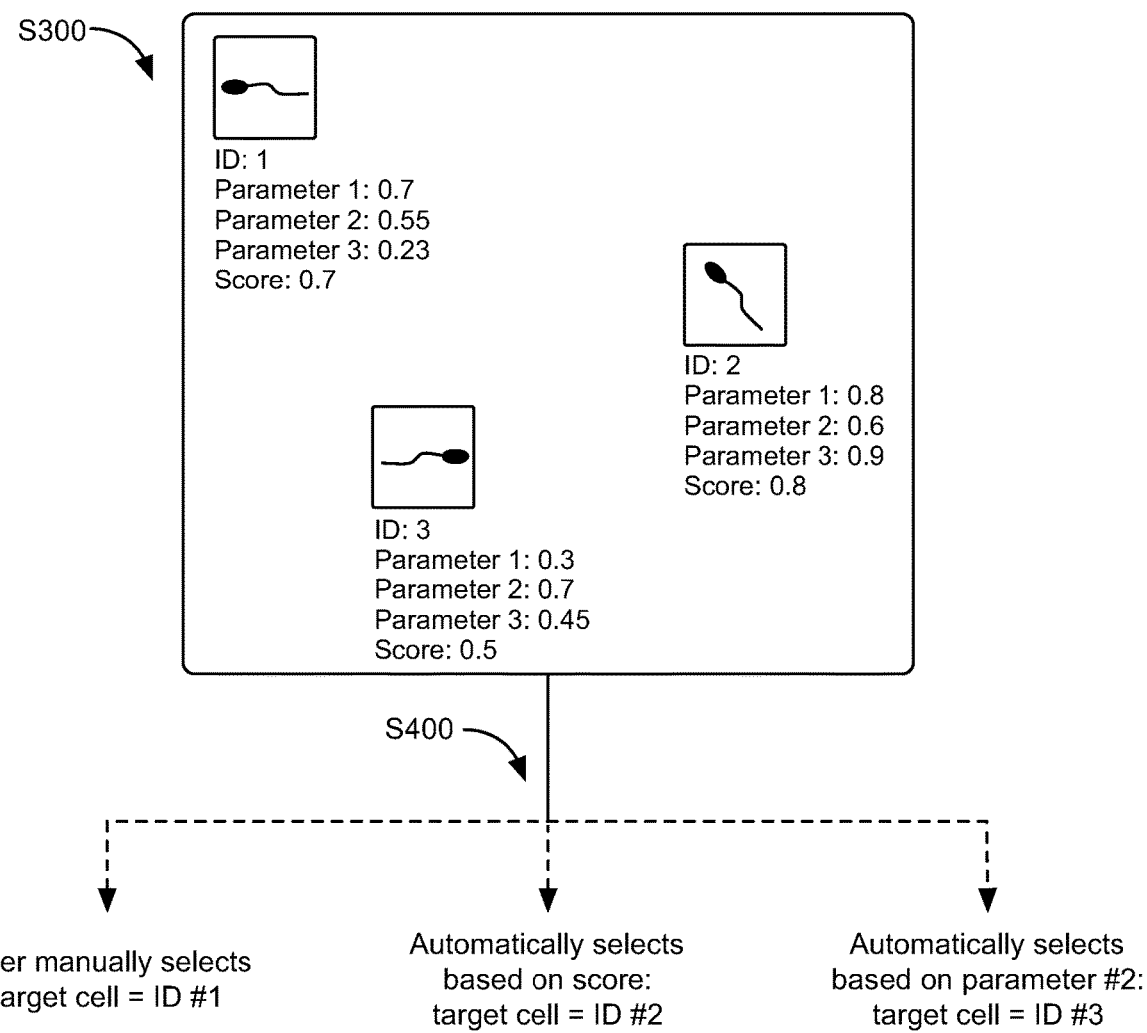
FIG. 4 depicts an illustrative example of gamete selection.

The gamete (e.g., a target gamete) can be selected automatically (e.g., based on the respective gamete attribute values, aggregated gamete attribute values, confidence scores, etc.), manually (e.g., wherein predicted attribute values are presented to a user for user selection; wherein the gamete is selected by a specialist; etc.), randomly, and/or be otherwise selected. The gamete can be selected using: a set of selection criteria, an equation (e.g., where gamete attribute values are variables in the equation), one or more selection models (e.g., a trained neural network), a ruleset or criteria, heuristics, decision trees, ranking algorithms, filters, and/or any other selection method. An example is shown in FIG. 4.

The gametes can be selected using a set of selection criteria and/or be otherwise selected. Examples of selection criteria can include: gamete ranking within the population (e.g., select the top N % of the gamete sample, such as the top 1%, 2%, 5%, 10%, a range therein, etc.); whether the gamete satisfies one or more thresholds (e.g., attribute value thresholds, aggregate attribute value thresholds, predetermined thresholds, population-defined thresholds, etc.); whether the gamete attribute values have a predetermined pattern, whether the gamete attribute value is within a predetermined set of included and/or excluded attribute classifications (e.g., head must be classified as "normal"; head must not be classified as "amorphous", neck must not be "sharply bent," etc.); gamete comparison against one or more reference gametes (e.g., other gametes in the sample); and/or any other selection criteria or combination thereof.

In a first variant, a predetermined number or percent of gametes in the set can be selected. In a second variant, gametes are selected based on one or more statistical measures of distributions for one or more gamete attributes aggregated over time. The statistical measure can be a measure of location (e.g., central tendency, mean, mode, interquartile mean, etc.), measure of statistical dispersion or spread (e.g., absolute deviation, standard deviation, variance, range, interquartile range, distance standard deviation, etc.), measure of distribution shape (e.g., skewness, kurtosis), measure of statistical dependence (e.g., correlation coefficient), and/or be otherwise defined. In a third variant, gametes associated with an attribute value confidence score less than a threshold are selected. In a fourth variant, a gamete is selected when the gamete has satisfied a condition (a threshold condition, a comparison condition, etc.) for a threshold period of time. In a fifth variant, the gamete (e.g., a target gamete) can be selected when it satisfies the selection criteria better than a previously selected gamete (e.g., a reference gamete). In a sixth variant, the gamete can be selected when the values for a set of key gamete attributes satisfy a predetermined set of conditions. The key gamete attributes can be: manually specified, learned (e.g., using SHAP values, feature correlation methods, feature selection methods, etc.), and/or otherwise determined. In a seventh variant, the gamete can be selected based on a decision tree. In an eighth variant, the gamete (e.g., a target gamete) can be selected when it satisfies a condition (e.g., a comparison condition, a threshold condition, etc.) relative to one or more reference gametes. In a ninth variant, a gamete is selected using a combination of selection criteria in a multi-stage selection (e.g., gamete candidates selected from a gamete population based on preliminary attribute values in a first iteration of S300, wherein the gamete candidates can then undergo a second selection based on second attribute values). In an example, this multi-stage attribute value determination can reduce computational load by using a first attribute model that is less computationally intensive than the second attribute model (e.g., the first model is a classical model and the second model is a trained machine learning model). In a tenth variant, the gamete can be selected using the manipulation system (e.g., physical selection and/or isolation). This variant can be performed: randomly, based on motility, based on density (e.g., be the gametes within a centrifuged pellet), and/or otherwise selected.

In examples, the gametes can be selected using the methods disclosed in U.S. application Ser. No. 17/871,665 filed 22 Jul. 2022. However, one or more gametes can be otherwise selected.

S400 can be performed once, iteratively performed, or performed any number of times.

In a first variant, S400 is performed once. In this variant, attribute values for a set of gametes are extracted from the video, wherein a subset of gametes are selected based on the respective attribute values. For example, gametes can be selected after: attribute values have been collected for a predetermined number of time windows (e.g., evaluation epochs), after a threshold number of gametes have been evaluated, and/or when any other condition is met.

In a second variant, S400 is iteratively performed. In this variant, a first gamete is selected from a first sub-population of gametes visible in a first set of sub-videos (e.g., using one or more of the selection variants discussed above). The first gamete is then tracked (e.g., across the physical scene via S500, to a new scene segment, during S600, during S700, etc.), wherein attribute values can be determined for new gametes appearing in the field of view. A second gamete can be selected (e.g., instead of the first gamete, to replace the first gamete, etc.) when the second gamete's values (e.g., individual values, aggregate values, etc.) satisfy the selection criteria better than the first gamete's. All or parts of the method can then be iteratively repeated (e.g., including repositioning the currently selected gamete) until a stop condition is met. Examples of stop conditions can include: a predetermined time duration is met, the same gamete or no new gametes been selected for a predetermined number of epochs, the selected gamete's attribute values satisfy a predetermined set of conditions, a user manually selects the selected gamete, a statistical measure of the second gamete's attribute value distribution better satisfies a selection criteria as compared to the first gamete's attribute value distribution, after a threshold number of gametes have been evaluated, and/or any other stop condition.

However, S400 can be repeated or not repeated in any other suitable manner.

Positioning the gamete within a target region S500 functions to move a gamete (e.g., to/towards the target region, to a target position within the target region, etc.), to keep the gamete within a field of view (e.g., near the center of the field of view), to keep the gamete in focus (e.g., for the user to watch/analyze the gamete, for the system to analyze the gamete in S400, etc.), and/or to position the gamete for reorientation (S600) and/or manipulation (S700). In specific examples, S500 functions to coarsely adjust position of the gamete (e.g., within a threshold distance of a target position), fine-tune a position of the gamete, and/or otherwise adjust gamete positioning.

S500 can be performed before, during, and/or after: S200 (e.g., positioning the gamete based on the gamete track, positioning the gamete while tracking the gamete, etc.), S400, S600 (e.g., repositioning the gamete before, during, and/or after reorientation), S700 (e.g., position the gamete for manipulation; reposition the gamete for retrieval after immobilization; repositioning the gamete after a first unsuccessful immobilization attempt for a second immobilization attempt; etc.), and/or at any other suitable time. S500 can optionally be performed iteratively with all or parts of the method (e.g., iteratively with S200 to position the gamete based on an updated track); in real time with S100 (e.g., real-time focus adjustment, real-time gamete centering, etc.), S200, S600, and/or S700 (e.g., manipulating the gamete while the position of the gamete in maintained within the target region); and/or at any other suitable time.

The gamete can be: the gamete selected in S400, a manually selected gamete, a randomly selected gamete, a gamete undergoing attribute value determination, and/or any other gamete in the cell container.

The target region and/or a target position (e.g., a set of coordinates at or near the center of the target region) can be determined relative to a field of view, relative to the manipulation system, relative to a reference position on the imaging system, relative to the scene, and/or be otherwise configured. In examples, the target region can be: a field of view, a region within a field of view, a focus region, a manipulation region (e.g., an immobilization region, a retrieval region, etc.), and/or any other region. In an illustrative example, the stage can be moved to maintain the gamete within the field of view or within a manipulation system's workspace. The target region can be predetermined, manually determined, dynamically determined (e.g., based on the manipulation system position), and/or otherwise determined.

The z-component of the target region (e.g., a range of z-coordinates) and/or a z-component distance between the gamete location (e.g., the current gamete location) and the target region can optionally be determined using a focus model. Additionally or alternatively, the z-component of the target region and/or the z-component distance between the gamete location and the target region can be iteratively determined (e.g., iteratively adjusting the z-component of the target region until a current focus level is within an acceptable range) and/or be predetermined (e.g., a known range of z-coordinates corresponding to the imaging system being in-focus).

The focus model can be or use: regression, classification, neural networks (e.g., CNNs, DNNs, etc.), rules, heuristics, equations (e.g., weighted equations, etc.), selection, instance-based methods, regularization methods (e.g., ridge regression), decision trees, Bayesian methods, kernel methods, probability, deterministics, genetic programs, support vectors, or any other suitable method. The input to the focus model can be one or more images of the gamete (e.g., a video and/or sub-video), imaging system information (e.g., objective lens information, focus range information, etc.), and/or any other suitable inputs. The output of the focus model (e.g., a focus level, a focus metric, a focus distance, a focus direction, etc.) can be discrete, continuous, a classification, numeric, binary, and/or otherwise configured. In a first example, the focus model output is a distance (e.g., including direction or not including direction) between the current gamete location (e.g., the location of the gamete head, the gamete tail, the center of the gamete, etc.) and the target region. In a second example, the focus model output is a binary classification (e.g., 'out of focus' or 'in focus'). In a third example, the focus model output is a multiclass classification (e.g., 'out of focus—gamete location is too high,' out of focus—gamete location is too low,' or 'in focus'). In a fourth example, the focus model output is a z-coordinate of the target region (e.g., a z-coordinate where the gamete would be in focus).

Figure 17:
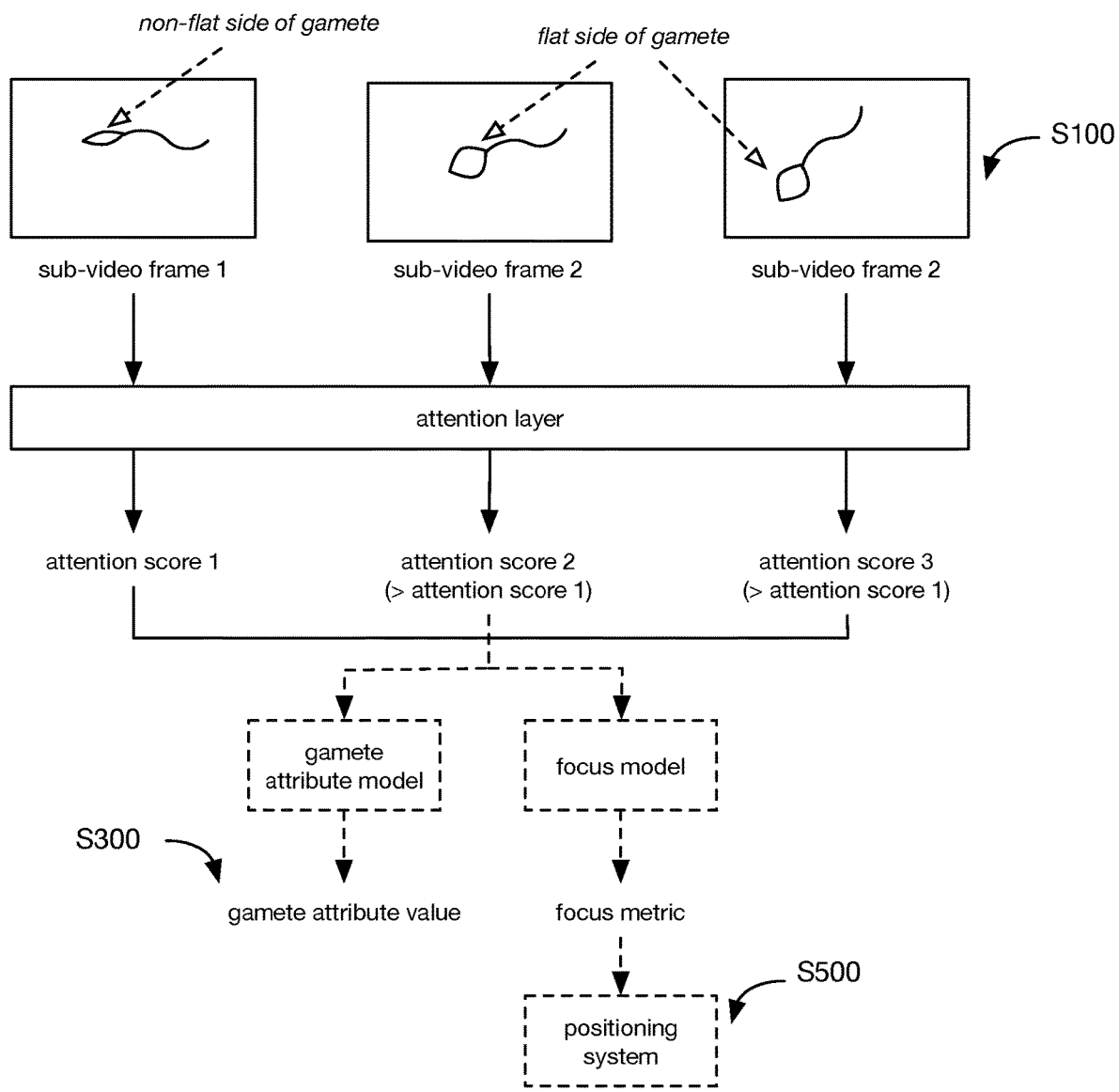
FIG. 17 depicts an illustrative example of an attention layer.

Optionally, the focus model input can be processed using an attention model, and/or the focus model can include a set of attention layers (e.g., to weight and/or select frames corresponding to a flat side of the gamete). For example, image inputs can be weighted and/or selected based on the gamete roll orientation (e.g., as described for the attribute model in S300). An example is shown in FIG. 17.

The focus model can be learned (e.g., using supervised learning, self supervised learning, unsupervised learning, transfer learning, etc.), fit, trained, predetermined, and/or can be otherwise determined. Training the focus model can optionally include acquiring images (e.g., training images) of a gamete in focus and out of focus, wherein the images are labeled (e.g., manually labeled, automatically labeled, etc.). The labels can optionally include a distance (e.g., distance out of focus), a direction (e.g., the direction out of focus), and/or any other information. In focus images are preferably images where the gamete head is in focus, but can additionally or alternatively be images where the gamete neck is in focus, the gamete tail is in focus, the overall gamete is in focus (e.g., the majority of the gamete is in focus), and/or be otherwise defined. In an illustrative example, a user manually focuses on the gamete (e.g., a static gamete) and in focus images are acquired. The gamete z-location is then adjusted (e.g., by manually or automatically actuating the imaging system stage in z-direction, by manually or automatically actuating the positioning system in the z-direction, etc.) to acquire out-of-focus images. In an example, the training images are acquired using static gametes with different roll orientations (e.g., wherein the training images include images depicting flat and side views of gamete heads). However, the focus model can be otherwise trained.

Positioning the gamete within the target region can include moving the gamete and/or the target region within a given reference frame (e.g., a static or dynamic reference frame associated with: the cell container, the scene, a field of view, a manipulation region, the imaging system, the positioning system, the manipulation system, the video scene, etc.). In variants, this can function to orient the gamete within, and/or maintain gamete location within, the target region. S500 is preferably performed by actuating the positioning system (e.g., sending actuation instructions to the positioning system, adjusting actuation instructions for the positioning system, etc.), but can additionally or alternatively be manually performed, performed by actuating the imaging system and/or the manipulation system (e.g., wherein the aspirator pushes the gamete towards a target position), and/or otherwise performed. The actuation instructions can be based on: the gamete track determined via S200, an actuator lag time, actuator constraints imposed by fluid shear, actuator translation limits, and/or any other suitable information. The actuation instructions can optionally be modified to smooth positioning system movements.

Figure 8:
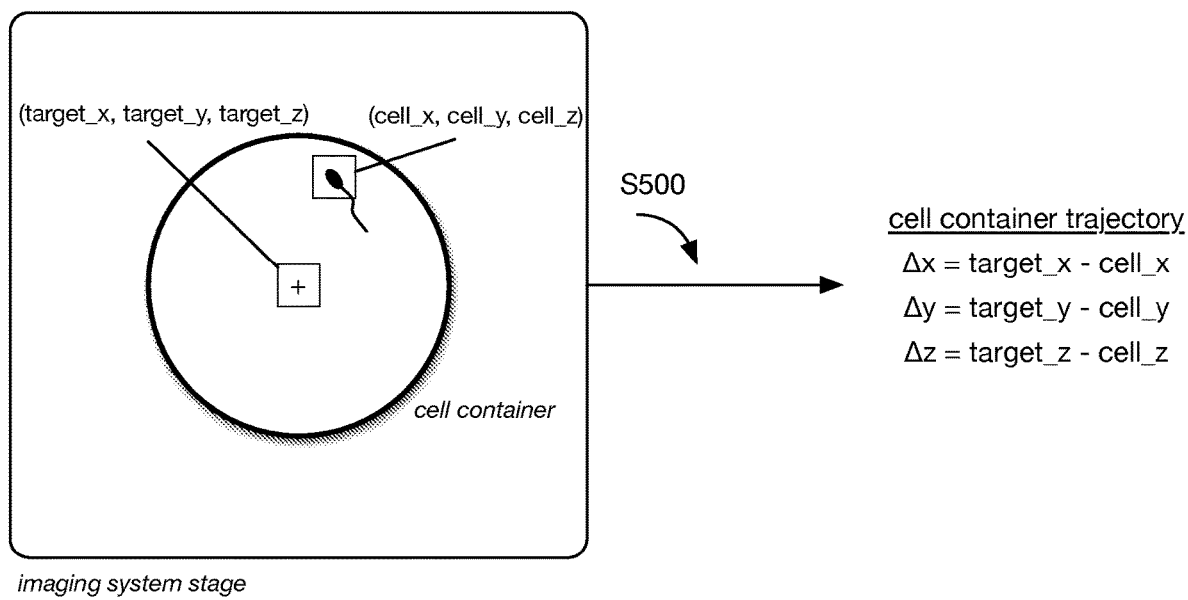
FIG. 8 is an illustrative example of the method, including gamete positioning.

In a first variant, S500 is performed by using a PID controller and/or any feedback loop mechanism. The controller can use tracking output information from S200 and/or S300 (e.g., a current or predicted location of the gamete) as input to generate or adjust actuator instructions. In one embodiment, a location error value is calculated based on a difference (e.g., a 3D vector difference and/or any delta representation) between the target region (e.g., a target position) and the current and/or predicted location of the gamete; example shown in FIG. 8. This location error is then fed into the controller to output actuator instructions such that the gamete is moved towards the target region. This loop can be performed at a frequency equal to, greater than, or less than the sampled video rate. S500 can additionally or alternatively be performed at a frequency based on the speed of the gamete and/or gamete type (e.g., 25-55 frames per second for sperm).

In a second variant, the platform is actuated to move based on a vector. The magnitude of the vector can be a predetermined distance (e.g., based on actuator constraints, imaging constraints, cell speed, etc.), a magnitude based on the gamete location (e.g., location relative to a target position), and/or any other magnitude. In a first embodiment, the vector has a direction based on the current or predicted gamete location and the target region (e.g., a target position in the region). In an example, this can preemptively move the cell container to a position that aligns a predicted gamete position within the target region, and/or ensure that the target region follows the gamete motion. In an illustrative example, when using a static coordinate system where target region is always centered at (0,0,0), if the gamete is currently located at (2,3,1), the positioning system will then move the cell container in a direction based on the vector [−2,−3,−1]. In a second embodiment, the actuator instructions instruct the positioning system to move the cell container opposite the gamete trajectory (e.g., where a gamete orientation attribute value can be representative of the gamete trajectory), and/or move the sensor (e.g., imaging system) along the gamete trajectory. This embodiment can optionally be performed when the gamete is within the target region (e.g., to maintain the gamete position relative to the target region).

In a third variant, S500 includes: determining a direction to move the gamete (e.g., to move the cell container); moving the gamete one or more steps in the determined direction; and repeating all or parts of S100-S300. These steps are then repeated based on the updated tracking information and/or gamete location information from S200 and/or S300. In a first embodiment, the distance the platform moves in one step is determined based on the iteration rate of the steps (e.g., if this loop occurs every frame of the video, the step distance is determined based on the frame rate). In a second embodiment, the step distance is determined based on the actuator speed.

In a fourth variant, the target region is associated with a field of view. The target region is then moved such that the center of the field of view is at or near the gamete position. In a first embodiment, the camera field of view includes the entire cell container while only portion of this field of view is displayed to a user; this smaller field of view includes the target region which moves with updated gamete position information (e.g., a field of view segment encompassing the gamete is presented to the user and/or provided to the system). In a second embodiment, the cell container is actuated as previously described, while the height of the target region is adjusted based on the gamete z-location (e.g., the focus of a camera and/or imaging system is shifted based on the gamete height). In a third embodiment, the camera and/or optics of the microscope can be moved to follow the gamete.

However, the positioning gamete can be otherwise performed.

The method can optionally include reorienting the gamete S600, which can function to orient the gamete for manipulation (e.g., when immobilization and/or retrieval is more efficient, ergonomic, or otherwise facilitated when the gamete is within a target orientation range). S600 can be performed after S100, after S500, during S500, before S700, after S730 (e.g., between immobilization and retrieval), and/or at any other suitable time. S600 can optionally be performed iteratively with all or parts of the method (e.g., iteratively with S200 to reorient the gamete based on an updated track, iteratively with S500, etc.); in real time with S100, S200, S500, S700 (e.g., manipulating the gamete while the orientation of the gamete in maintained within a target orientation range); and/or at any other suitable time. S600 can optionally be part of S500 (e.g., wherein S500 additionally includes orienting the gamete in the target pose) or separate from S500 (e.g., sequential with S500).

S600 can be performed by: the manipulation system, the positioning system, the imaging system, a user, a combination thereof, and/or any other system. The reorientation is preferably performed in a horizontal plane (e.g., xy plane), but can alternatively be performed in any other plane.

S600 can include reorienting the gamete to satisfy one or more orientation criteria relative to a target orientation. The orientation criterion can be: the gamete orientation (e.g., the primary axis of the gamete tail and/or any other orientation attribute value) matches the target orientation, the gamete orientation is within a threshold range of the target orientation, and/or any other orientation criterion. The threshold range can be between −90°-90° or any range or value therebetween (e.g., −45°-45°, −20°-20°, −10°-10°, −5°-5°, 0-45°, etc.), but can alternatively be less than −90° or greater than 90°. The target orientation and/or the orientation criterion (e.g., the acceptable range relative to the target orientation) can be determined based on (e.g., relative to) the manipulation system (e.g., number of degrees of freedom of manipulation system actuation, range of motion of the manipulation system, pose of the manipulation system, a manipulation system reference, etc.), the imaging system (e.g., the target orientation is determined relative to a field of view reference), based on the gamete pose (e.g., the location of the gamete head, the location of the gamete relative to the manipulation system, etc.), be predetermined (e.g., within a threshold range of a predetermined orientation relative to the scene), and/or any other suitable information. In a first example, the target orientation can be a predetermined angle relative to the manipulation system (e.g., the gamete orientation is orthogonal to a manipulation system component). In a second example, a range of acceptable target orientations can be determined such that an estimated manipulation system motion (e.g., a gamete immobilization swipe in S730 from a cut start point to a cut end point, any other motion used in all or parts of S700, etc.) is within the range of manipulation system capabilities (e.g., based on the degrees of freedom of the manipulation system actuation) and/or does not intersect within a threshold distance of the gamete's head. In a third example, the target orientation can include positioning the gamete with the gamete tail proximal the manipulation system and/or with the gamete head positioned distal (e.g., away from) the manipulation system. However, any other target orientation can be used.

S600 can optionally be based on an orientation attribute value (e.g., a detected, estimated, or predicted gamete orientation). In an example, S600 includes: determining a gamete orientation (e.g., via S300 methods), comparing the gamete orientation to the target orientation, determining whether the gamete satisfies the orientation criterion based on the comparison, and reorientating the gamete (e.g., iteratively reorienting the gamete) until the orientation criterion is satisfied. In a first specific example, S600 includes: determining a gamete's pose (e.g., in a global frame of reference, relative to the manipulation system, etc.), determining the difference between the gamete's pose and a target pose (e.g., angular difference, distance, etc.), and actuating a system (e.g., the positioning system and/or the manipulation system) to rotate the gamete, such that the gamete's pose substantially matches the target pose (e.g., within a threshold range). In a second specific example, S600 includes: determining a gamete's pose (e.g., in a global frame of reference, in a local reference frame, etc.), determining that the gamete's pose does not satisfy the orientation criterion, and iteratively actuating a system (e.g., the positioning system and/or the manipulation system) to adjust the gamete orientation until the orientation criterion is satisfied. Actuation instructions used in S600 can be determined based on the gamete pose, based on difference between the gamete's pose and the target pose, be predetermined (e.g., a predetermined motion of the manipulation system), a combination thereof (e.g., a predetermined manipulation system motion executed at a location determined based on the gamete's pose), and/or be otherwise determined. However, S600 can be otherwise performed.

Figure 6A:
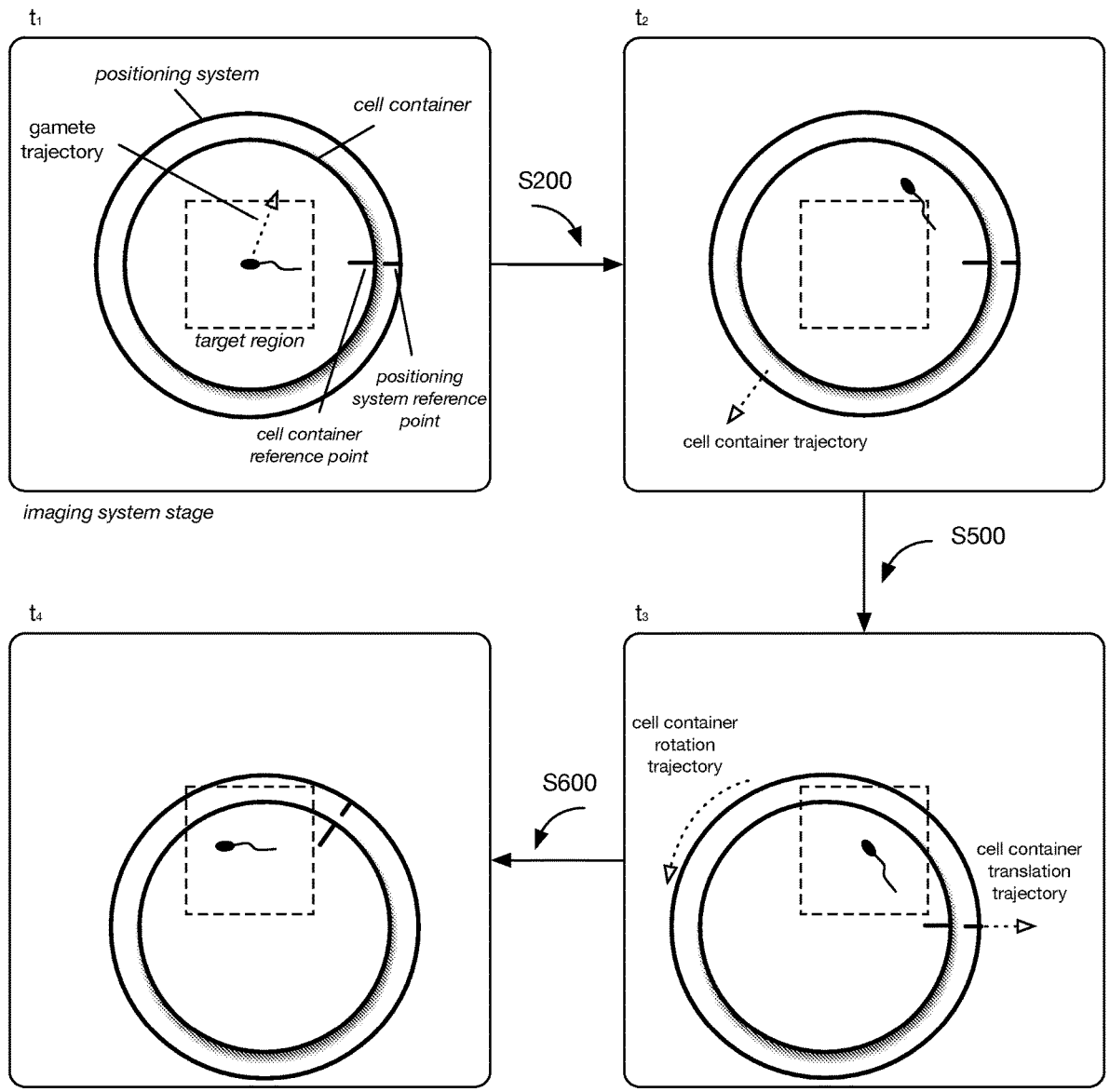
FIGS. 6A and 6B depict examples of repositioning and reorienting the cell container.
Figure 6B:
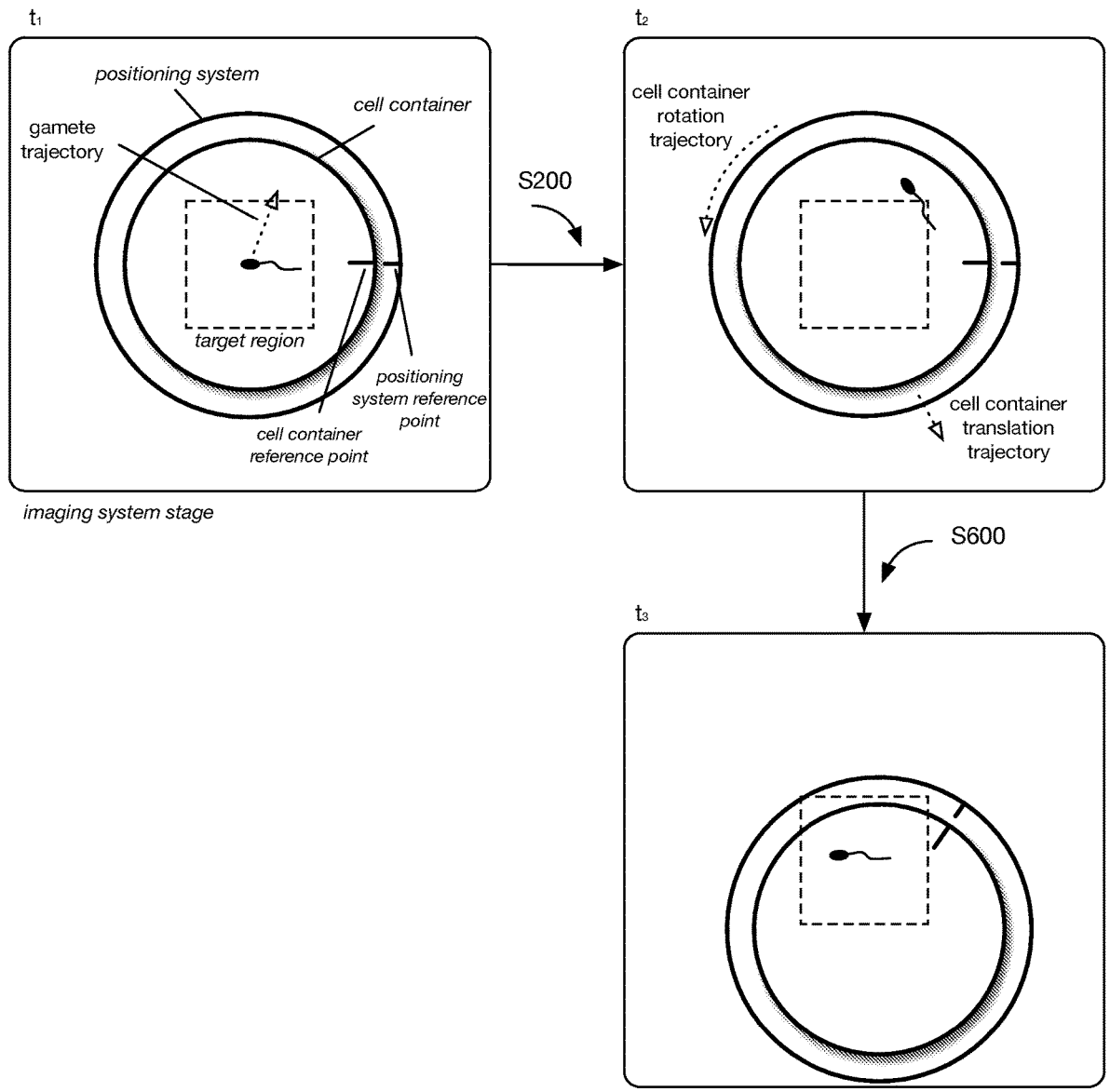
Figure 7:
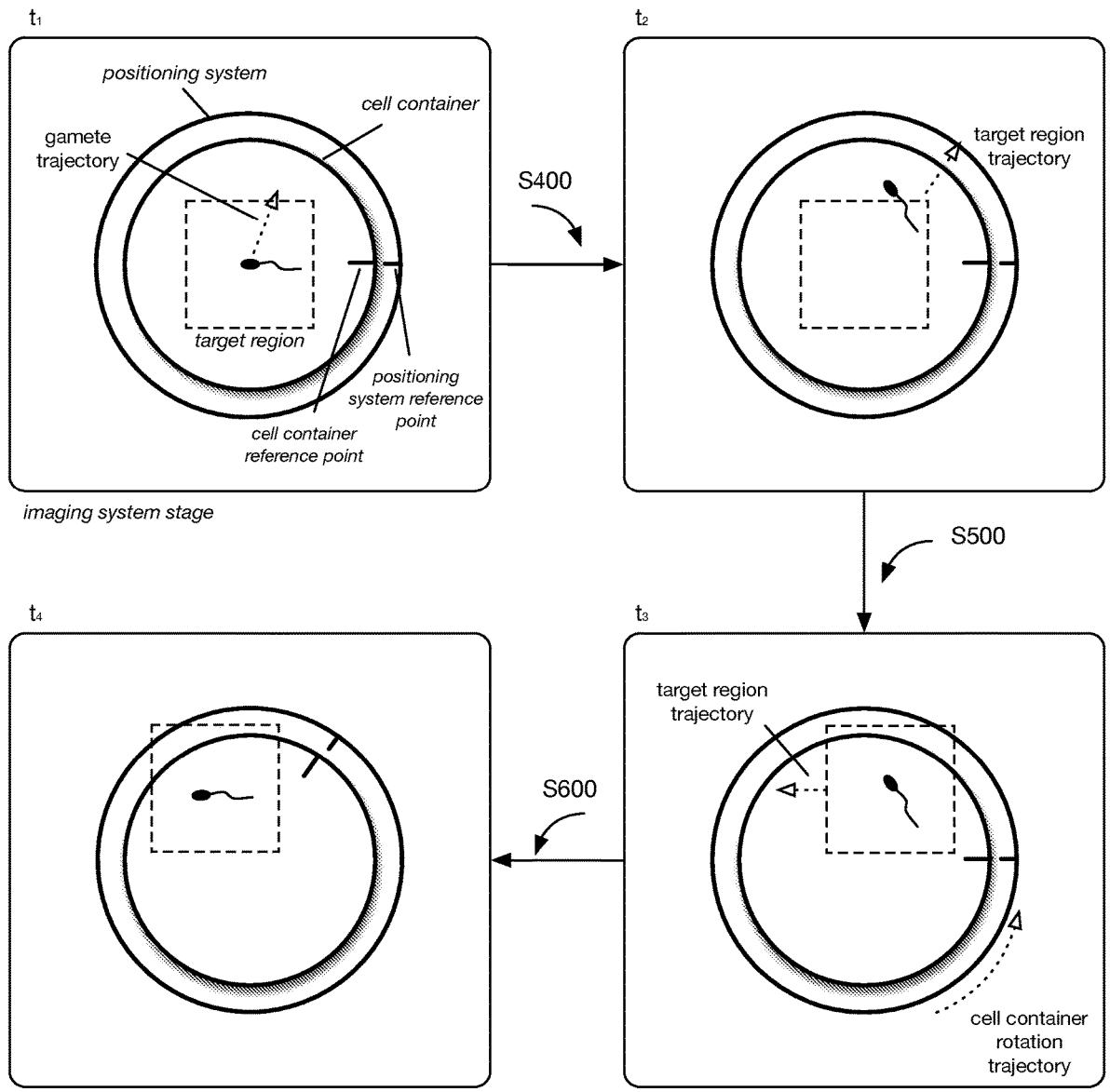
FIG. 7 depicts an example of repositioning the target region.
Figure 9:
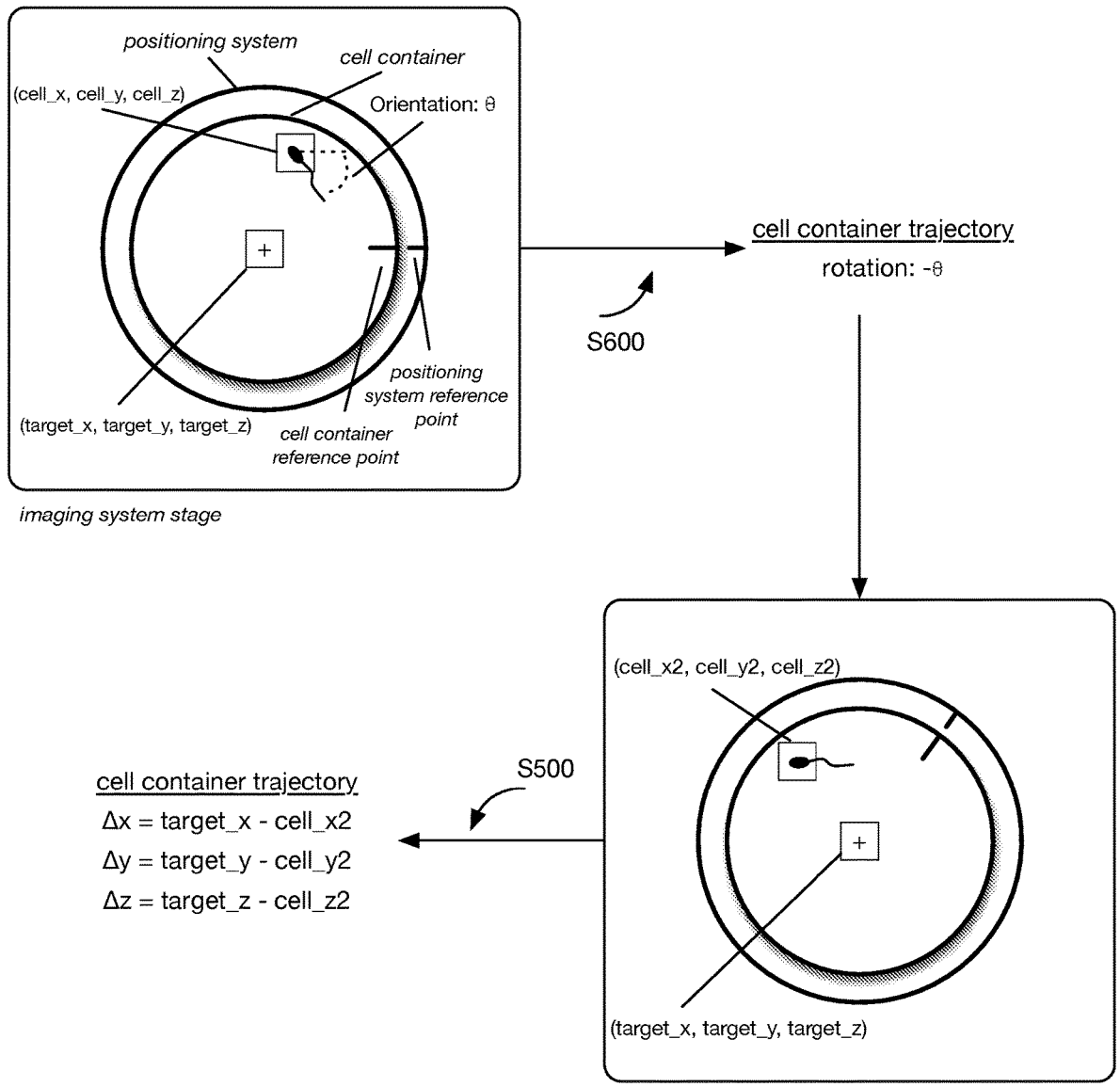
FIG. 9 is an illustrative example of the method, including gamete reorientation.

In a first variant, reorienting the gamete can include actuating the positioning system (e.g., the same positioning system used in S500 and/or a different system). In a first embodiment, the positioning system includes a platform that can be rotated such that the gamete is reoriented towards the target orientation. In a second embodiment, reorientation includes both rotation and translation of the platform and/or cell container; examples shown in FIG. 6A, FIG. 6B, and FIG. 7. Rotation can be performed about any axis (e.g., a z-axis extending from the gamete location, from a platform center, etc.). Given that rotating the positioning system may alter the location of the gamete, translation can be performed to accommodate for this position alteration. In an example of this second embodiment, S600 can be performed concurrently with S500 such that the rotation and translation occur to position and orient the gamete towards a target position and target orientation (e.g., based on a current or predicted gamete location and orientation). This can be performed in one step (e.g., calculating the actuation instructions for translation and rotation based on the axis of rotation) or multiple steps (e.g., performing a rotation followed by a translation or vice versa); example shown in FIG. 9.

Figure 5:
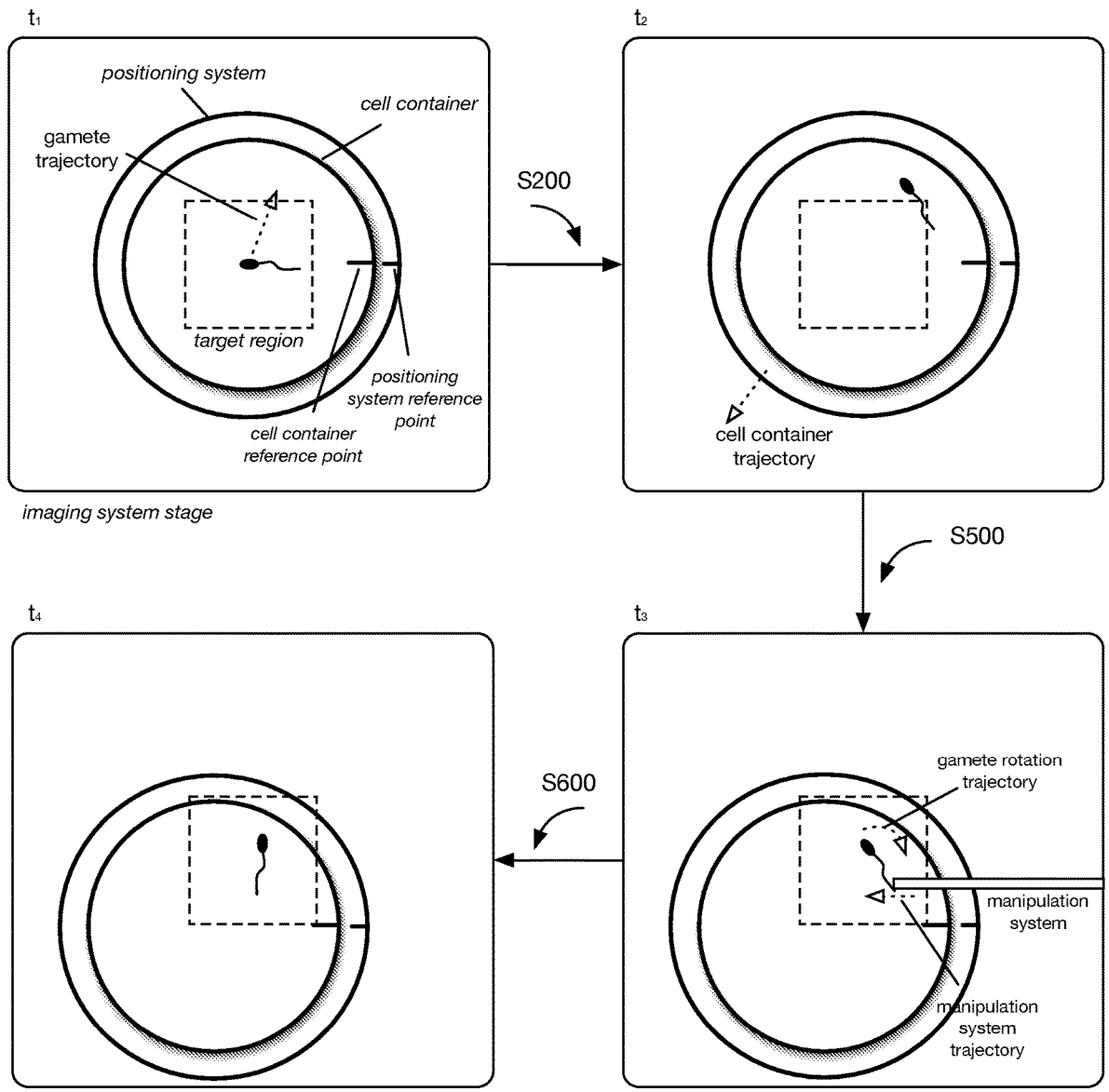
FIG. 5 depicts an example of repositioning the cell container and reorienting the gamete within the cell container.
Figure 10A:
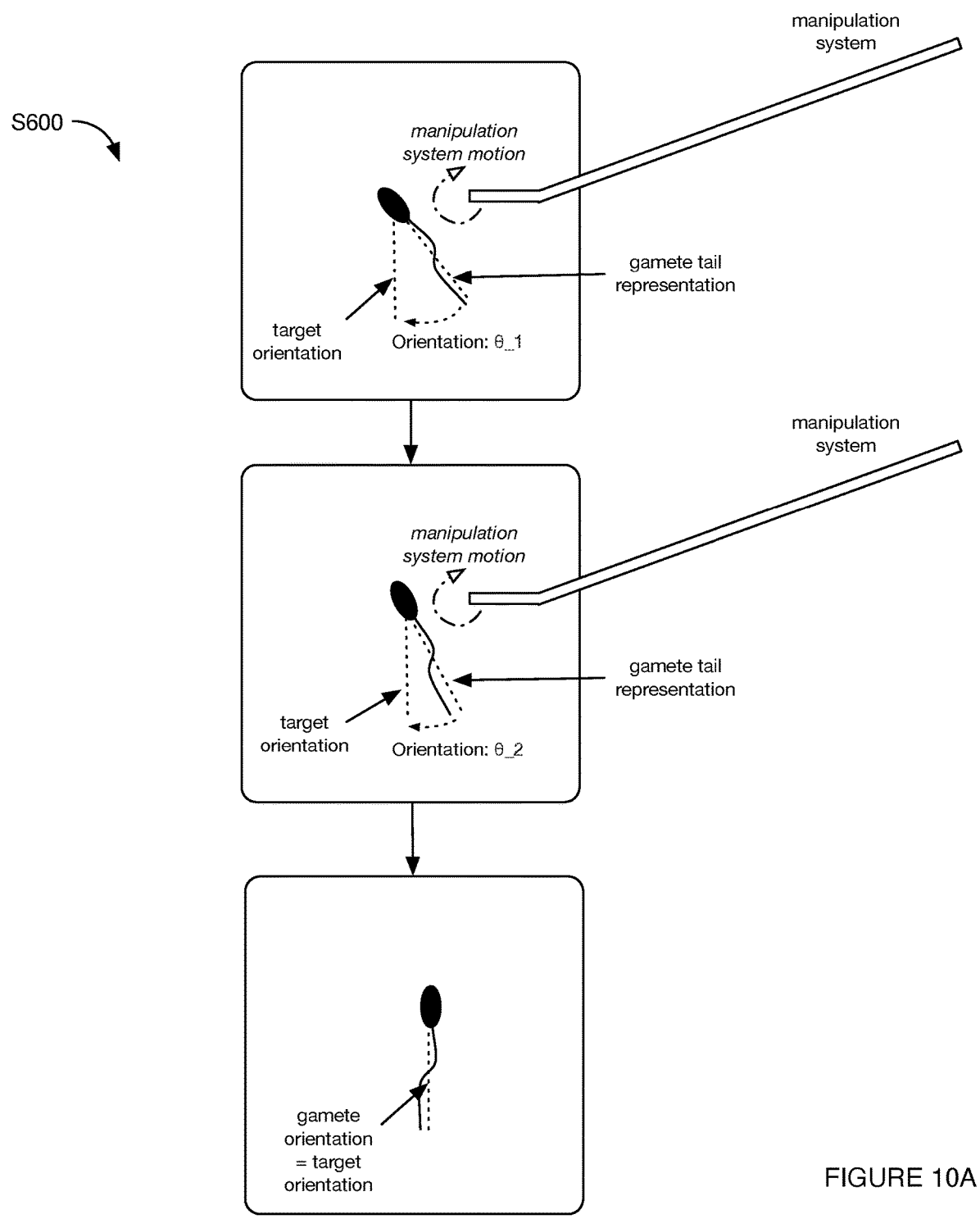
FIG. 10A is a first illustrative example of reorienting a gamete using a manipulation system.
Figure 10B:
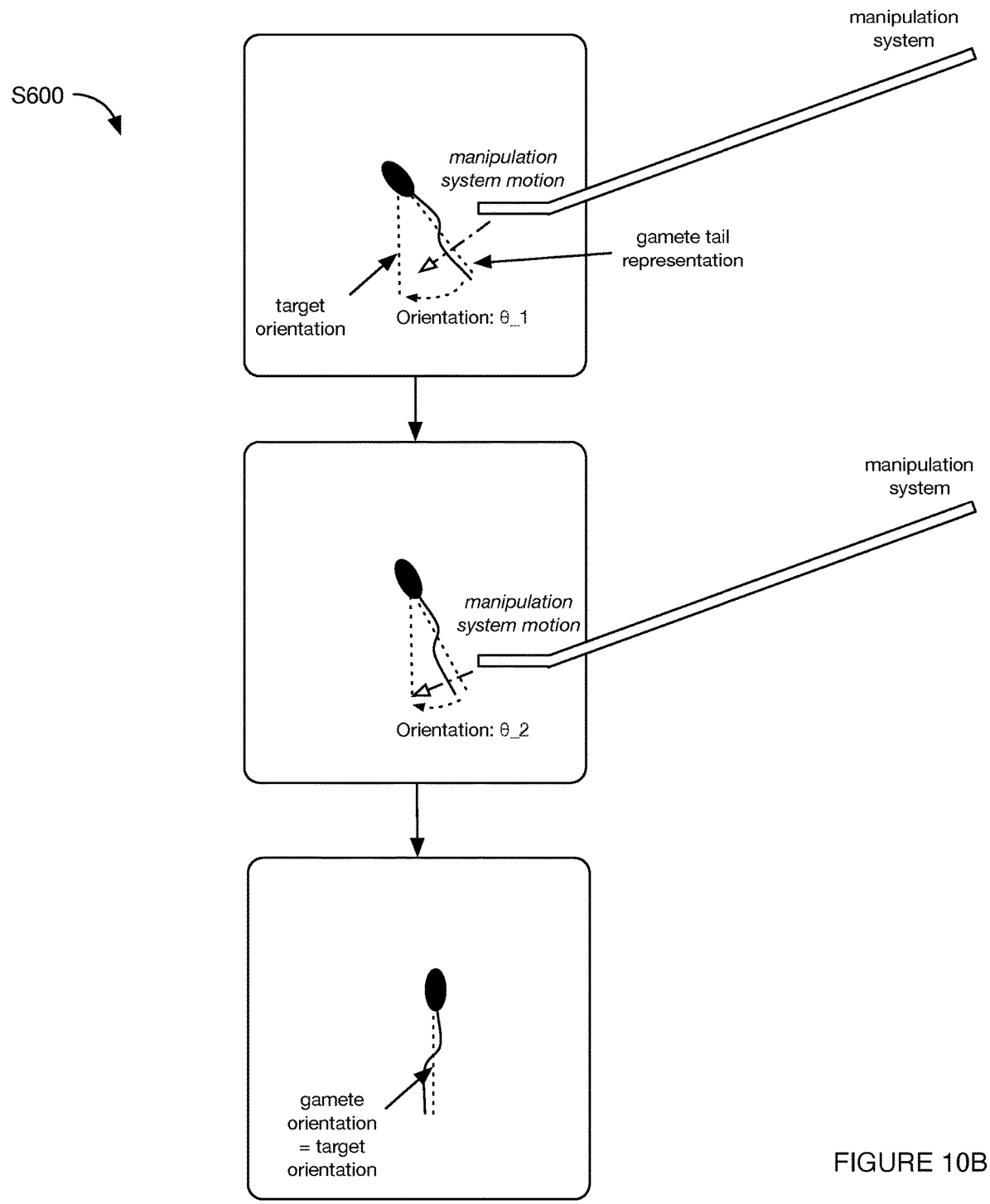
FIG. 10B is a second illustrative example of reorienting a gamete using a manipulation system.

In a second variant, the gamete can be reoriented using the manipulation system (e.g., reoriented within a stationary cell container, reoriented within a cell container while the cell container is dynamically repositioned to center the gamete, etc.). An example is shown in FIG. 5. For example, the manipulation system (e.g., immobilization system, retrieval system, etc.) can be used to physically guide the gamete reorientation by pushing (e.g., nudging) the gamete and/or moving fluid near the gamete. The manipulation system can push the gamete and/or move fluid at or near the gamete head, the gamete neck, the gamete tail, and/or any other location on or near the gamete. In a first example, the manipulation system can physically contact (e.g., touch, nudge, push, etc.) the gamete. In this example, the manipulation system preferably does not physically contact the gamete head (e.g., the manipulation system contacts the tail), but can additionally or alternatively contact the gamete head. An example is shown in FIG. 10B. In a second example, the manipulation system can generate fluid motion (e.g., a fluid vortex, any linear and/or rotational fluid motion, etc.) by moving near the gamete. In this example, the manipulation system preferably does not physically contact the gamete, but can additionally or alternatively contact the gamete (e.g., contacting the tail, not contacting the head, etc.). In specific examples, the tip of an aspirator (e.g., an ICSI or IMSI needle and/or micropipette) moves along a horizontal rotational path (e.g., a circular path in the xy plane), a vertical rotational path (e.g., a circular path in the xz and/or yz plane), a linear path, a combination thereof, and/or any other motion path. The manipulation system path of motion can optionally be based on the gamete location (e.g., the start point of the path is based on the gamete location), the target orientation, the gamete orientation (e.g., the direction and/or degree of motion is based on the gamete orientation and/or the difference between the gamete orientation and the target orientation), predetermined (e.g., the same path, iteratively used until the orientation criterion is satisfied), and/or otherwise determined. An example is shown in FIG. 10A. In a third example, the manipulation system can inject and/or aspirate fluid near the gamete (e.g., adjacent to the gamete head and/or tail). The amount of fluid, fluid pressure, and/or any other fluid parameter can optionally be based on the gamete orientation and/or the target orientation (e.g., based on the difference).

In a third variant, the cell container remains in place while a system (e.g., positioning system, imaging system, manipulation system, etc.) is actuated (e.g., translated, rotated, angled, moved in 1D to 6D, etc.), such that the gamete is reoriented relative to a frame of reference associated with the system.

In a fourth variant, the field of view (e.g., containing the target region) is rotated in response to the orientation of the gamete. In an example, the gamete remains in a static orientation relative to all or parts of the system while a video of the gamete (e.g., a displayed video feed) is reoriented such that the gamete orientation matches a target orientation.

In a fifth variant, an electric and/or magnetic field can be used to reorient one or more systems, the cell container, the gamete within the cell container, and/or any other component.

However, the gamete can be otherwise reoriented.

The method can optionally include manipulating the gamete S700. S700 can function to prepare the gamete for retrieval, retrieve the gamete, and/or otherwise manipulate the gamete. S700 can be performed after S500, after S600, in response to detection that the gamete is within a target region (e.g., a manipulation region) and/or within a target orientation range, in response to a user input, in response to another manipulation event (e.g., retrieval S760 can be performed in response to immobilization S730 and/or in response to re-identifying the gamete after immobilization S750), and/or at any other suitable time.

S700 can include immobilizing the gamete, reidentifying the gamete, retrieving the gamete, injecting the gamete, attaching accessory structures to the gamete, and/or any other manipulation. S700 can be performed by one or more manipulation systems, manually, and/or by any other suitable system.

S700 can optionally include immobilizing the gamete S730, which can function to facilitate isolation and/or retrieval of the gamete. Immobilizing the gamete can include partially or fully immobilizing the gamete using a manipulation system. Optionally, immobilization can occur only when an area near the gamete (e.g., in the path of an estimated manipulation system motion) is free of other cells (e.g., viable and/or nonviable gametes; only free of viable gametes; etc.).

S730 can include: determining a target immobilization point (e.g., a pinning point, a cut point, a cut start point, a cut end point, etc.) and/or target immobilization axis (e.g., a pinning axis, a cut axis, etc.); and executing the gamete immobilization based on the target immobilization point and/or target immobilization axis.

The target immobilization point can be a location (e.g., coordinates) on the gamete contacted by the manipulation system (e.g., a gamete location affected by manipulation system pinning and/or manipulation system swiping); a position on the gamete (e.g., a position along the tail that is a predetermined distance from the neck); a location to position the manipulation system (e.g., the tip of the ICSI needle) before, during, and/or after executing the gamete immobilization (e.g., a set of waypoints); and/or otherwise defined. The target immobilization axis can be a path the manipulation system follows before, during, and/or after executing the immobilization; an axis connecting two target immobilization points (e.g., a cut start point and a cut end point); an axis relative to a gamete orientation; and/or otherwise defined. The immobilization axis can optionally include a direction (e.g., a cut direction). The target immobilization point and/or the target immobilization axis can be defined relative to a static and/or dynamic reference frame (e.g., reference frame associated with: the video scene, the field of view, a target region and/or target orientation, a manipulation region, the imaging system, the positioning system, the cell container, one or more principal axes of the gamete, a reference image, etc.).

The target immobilization point and/or the target immobilization axis can be determined based on: videos, sub-videos, and/or images of the gamete; attribute values for the gamete (e.g., orientation attribute value, gamete location, gamete trail attribute value, etc.); the manipulation system parameters (e.g., number of degrees of freedom, manipulation system motion parameters, etc.); cell container parameters (e.g., a known z-location of the cell container base); and/or any other information. The target immobilization point and/or the target immobilization axis are preferably determined using segmentation methods, object detection methods, image segmentation methods, heuristics, filters, attribute models, and/or other methods.

The target immobilization axis is preferably determined based on a gamete attribute value (e.g., an orientation attribute value, a gamete tail representation, etc.), but can additionally or alternatively be determined based on the target orientation (e.g., a predetermined angle relative to the target orientation), one or more target immobilization points (e.g., the axis intersects with a target immobilization point, the axis connects two or more target immobilization points, etc.), the gamete video (e.g., a model that outputs the target immobilization axis based on gamete videos, sub-videos, and/or images), and/or otherwise determined. For example, the target immobilization axis can be orthogonal relative to the gamete orientation (e.g., a gamete orientation attribute value, the principal axis of the gamete tail, etc.), within a threshold angle relative to the gamete orientation, and/or have any relationship to the gamete orientation. The threshold angle can be between 0° to 180° or any range or value therebetween (e.g., 20° to 160°, 30° to 150°, 40° to 140°, 50° to 130°, 60° to 120°, 70° to 110°, 80° to 100°, 90°, etc.), but can alternatively be less than 0° or greater than 180°. A direction associated with the target immobilization axis (e.g., a cut direction, wherein the manipulation system moves in the cut direction along the immobilization axis during immobilization) can be predetermined, determined based on the manipulation system pose relative to the gamete pose, determined based on the gamete head location relative to the gamete tail location (e.g., wherein the cut direction is selected such that the gamete moves away from the gamete head), and/or otherwise determined. For example, the cut direction can be: top down, bottom up, start from a point closer to the head and end at a point further from the head, start from a point distal the head and end at a point proximal the head, be randomly determined, be predicted by a trained model (e.g., a neural network trained to predict a cut path and/or direction that minimizes a probability of touching or affecting the head), be determined based on the direction of the motor actuating the manipulation system, be manually determined, and/or be otherwise configured.

The target immobilization point x-coordinate and/or y-coordinate are preferably determined based on a gamete tail representation (e.g., a mask of the gamete tail, a function fit to a mask of the gamete tail, etc.; determined via S300 methods) and/or any other gamete attribute value, but can additionally or alternatively be determined based on other target immobilization points, the target immobilization axis, the gamete video (e.g., a model that outputs the target immobilization point based on gamete videos, sub-videos, and/or images), and/or otherwise determined. For example, a cut point (e.g., the xy coordinates of the location on the gamete tail that is contacted by the manipulation system) is preferably the middle of the gamete tail, but can alternatively be a distance along the tail (e.g., from the neck base, from the head base, from a head centroid, from the tail tip, from another gamete reference, etc.) and/or any other location on the gamete tail. The distance along the tail can be calculated (e.g., based on tail oscillation frequency, tail oscillation amplitude, angle between the tail and head, etc.), predetermined, manually determined, and/or otherwise determined. For example, the distance can be larger for gametes with sharper angles between the head and tail axis, and be shorter for gametes with shallower angles between the head and tail axis. The predetermined distance along the tail (e.g., starting at the head centroid) can be between 0 µm-60 µm or any range or value therebetween (e.g., 10 µm, 20 µm, 30 µm, 40 µm, 50 µm, etc.), but can alternatively be greater than 60 µm. The predetermined distance along the tail can additionally or alternatively be defined relative to the length of the gamete (e.g., entire length of the gamete including the gamete head), wherein the predetermined distance can be between 1/10-9/10 the length of the gamete or any range or value therebetween (e.g., 1/4 the length of the gamete, 1/2 the length, 3/4 the length, etc.), but can alternatively be less than 1/10 the length of the gamete or greater than 9/10 the length of the gamete.

Figure 13:
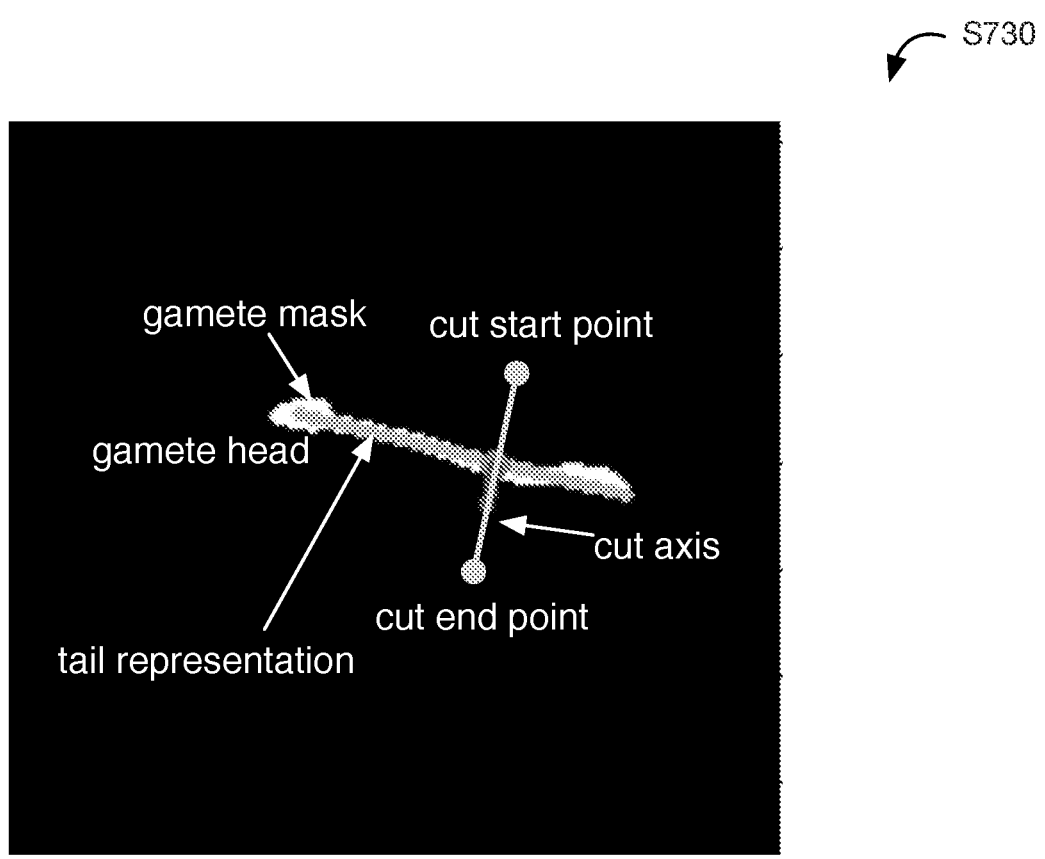
FIG. 13 depicts an example of target immobilization points and a target immobilization axis for immobilizing a gamete.

In a specific example, a cut start point and a cut end point (e.g., the xy coordinates of the starting and ending points of an immobilization swipe by the manipulation system) can be determined based on the cut point, the cut axis, and/or the cut direction. In an illustrative example, a gamete tail representation (e.g., a mask of the gamete tail) is used to determine a cut point on the gamete tail $(CP_x, CP_y)$ and a unit vector $N=(N_x, N_y)$ in the cut direction (e.g., orthogonal to the gamete orientation). The cut start point is then defined as $CS=(CS_x, CS_y)=(CP_x, CP_y)+alpha*(N_x, N_y)$ and the cut end point is defined as $CE=(CE_x, CE_y)=(CP_x, CP_y)-alpha*(N_x, N_y)$, wherein alpha is a parameter (e.g., a number of pixels). Alpha can be predetermined, learned (e.g., adjusted/trained based on immobilization success), and/or otherwise determined. Optionally, the cut direction, cut start point, and/or cut end point can be determined based on the orientation of the manipulation system (e.g., when the needle bore is parallel to the x-axis, the cut start point and the cut end point can be assigned such that the swiping motion is in the positive x direction with $CE_x$ greater than $CS_x$), based on the target immobilization point (e.g., wherein the cut start point is the immobilization point), and/or otherwise determined. An example is shown in FIG. 13.

The target immobilization point z-coordinate is preferably the base of the cell container and/or a predetermined distance from the base of the cell container, but can alternatively be the z-coordinate of a gamete location and/or otherwise determined. The predetermined distance can be 0 mm-2 mm or any range or value therebetween (e.g., 0.05 mm, 0.1 mm, 0.2 mm, 0.3 mm, 0.4 mm, 0.5 mm, 1 mm, etc.), but can alternatively be greater than 2 mm. In a first embodiment, the target immobilization point z-coordinate can be determined using a force gauge (e.g., connected to the manipulation system) to detect the bottom of the cell container. In a second embodiment, the target immobilization point z-coordinate can be determined by first moving the manipulation system in the x-direction and/or y-direction at a z-position above the bottom of the cell container, then moving the manipulation system in the x-direction and/or y-direction at sequentially lower z-positions until the x- and/or y-movement is impaired. In a third embodiment, the target immobilization point z-coordinate can be determined by estimating the location of the bottom of the plate (e.g., based on a pattern printed or projected onto the plate, using computer vision, using a depth measurement, etc.). In a fourth embodiment, the target immobilization point z-coordinate can be determined based on the z-coordinate of the gamete location (e.g., wherein the gamete location can be determined using S200/S300 methods).

Executing the immobilization can be performed one or more times (e.g., one or more immobilization attempts, until successful gamete immobilization is confirmed). Subsequent immobilization attempts can use the previously-determined target immobilization point(s) and/or target immobilization axis, or use newly determined target immobilization point(s) and/or a target immobilization axis. The immobilization can optionally be executed while the positioning system continues to maintain the gamete position (e.g., roughly maintain the gamete position within the target region using S500 methods) and/the gamete orientation (e.g., using S600 methods). The immobilization is preferably performed based on the planned cut (e.g., the cut point, the cut start and end points, the cut path, the cut waypoints, etc.), but can alternatively be performed based on other information. In a first variant, executing the immobilization includes actuating the manipulation system to pin the gamete (e.g., to bottom of the cell container) and swipe across the gamete tail, wherein swiping across the gamete tail physically damages the tail (e.g., nicking, kinking, breaking, cutting, etc.) and/or causes a biological response in the gamete such that the gamete is partially or fully immobilized. In a second variant, executing the immobilization includes actuating the manipulation system to pin the gamete along the target immobilization axis, wherein the gamete is pinned with sufficient force to physically damage the tail and/or cause a biological response in the gamete such that the gamete is partially or fully immobilized (e.g., with or without continued physical pinning). In a third variant, executing the immobilization includes lasering the gamete at the cut point (e.g., wherein the manipulation system is a laser). Lasering the gamete can optionally be performed without pinning, swiping, and/or reorientating the gamete. The laser can optionally be focused through the imaging system objective lens or focused through another (separate) set of optics. For example, the laser can be loaded directly in the objective lens, coupled to the objective lens optical path through another path (e.g., fluorescence microscopy path), and/or otherwise focused through the objective lens. The laser can be operated (e.g., powered on, steered, etc.) manually and/or automatically. In a first specific example, the positioning system (e.g., stage) can be actuated in one or more directions (e.g., after turning on the laser) such that the laser intersects with the gamete tail at the cut point. In a second specific example, the laser can be steered (e.g., by actuating a mirror) such that it intersects with the tail of the gamete at the cut point. However, the gamete can be otherwise immobilized.

Figure 14:
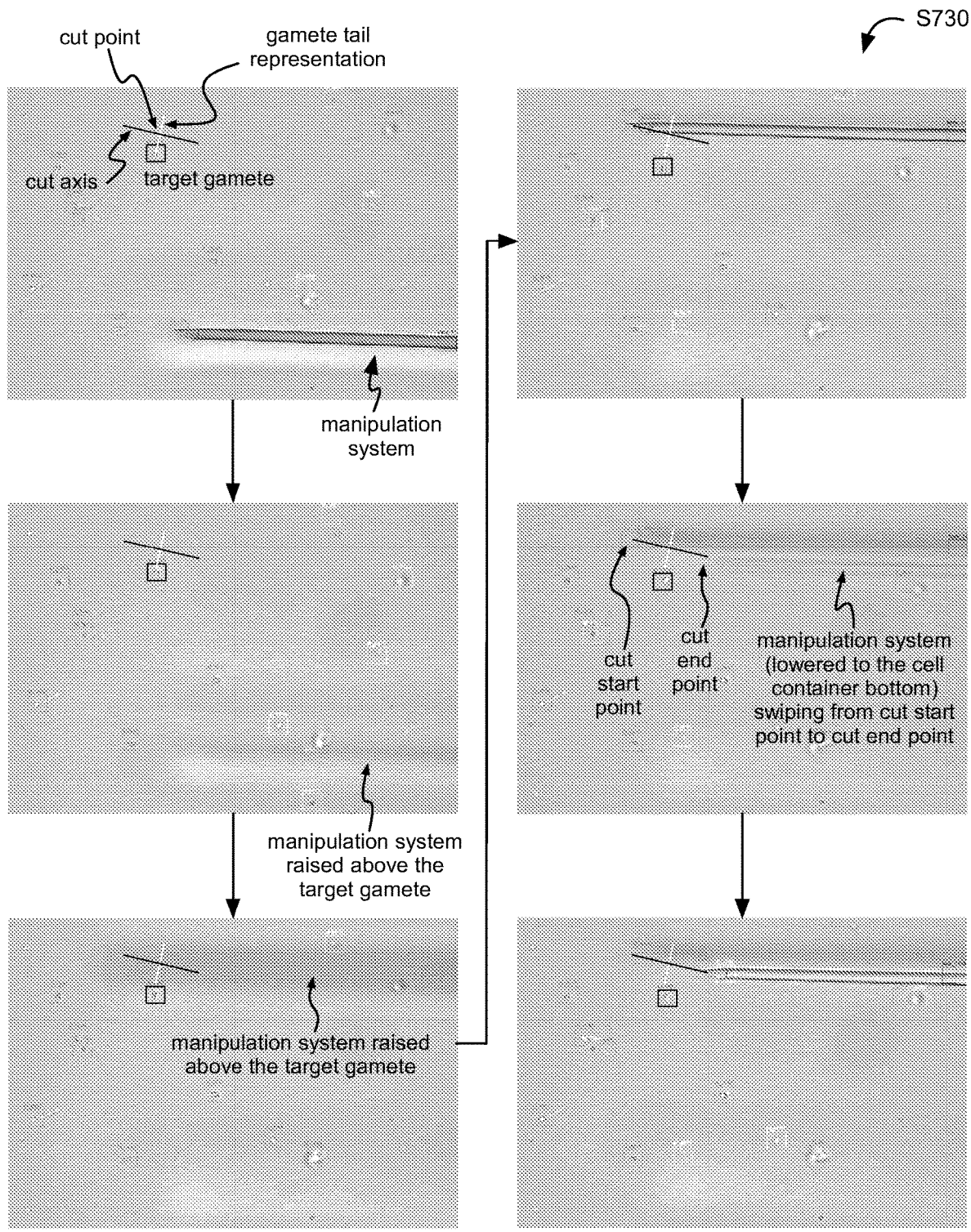
FIG. 14 depicts an illustrative example of immobilizing a gamete.

Pinning the gamete can include lowering the manipulation system in the z-direction and/or raising the gamete (e.g., the cell container) in the z-direction. In a first example, the manipulation system is lowered onto a motile gamete while the positioning system continues to maintain the gamete position in the x- and y-directions (e.g., and optionally the gamete orientation). In a second example, the gamete is moved (e.g., raised) towards the manipulation system (e.g., via S500 wherein the target region includes the z-coordinates of the manipulation system). In a first embodiment, the manipulation system can be an aspirator (e.g., needle) positioned with the bore of the aspirator substantially parallel to the plane of the cell container bottom and nonparallel (e.g., orthogonal, orthogonal within a threshold, etc.) to the gamete tail, wherein the aspirator bore presses down across the gamete tail to pin the gamete. In a second embodiment, the manipulation system can be an aspirator arranged with the bore of the aspirator substantially orthogonal to the plane of the cell container bottom, wherein the gamete head is positioned at the aspirator opening (e.g., wherein the edge of the aspirator opening does not contact the head) and the aspirator presses down on the tail to pin the gamete to the cell container (e.g., with the gamete head within the aspirator bore), such that the aspirator clips the gamete tail while aspirating. In an illustrative example of pinning a gamete, the manipulation system can be raised in the z-direction above the gamete while moving the manipulation system (e.g., the tip of the aspirator) to the x- and y-coordinates of a target immobilization point (e.g., the cut start point). The location of the manipulation system can optionally be determined by averaging the detected location across multiple images when the tip is in focus. The manipulation system can then be lowered to a z-coordinate (e.g., z-coordinate of the target immobilization point) at or near the bottom of the cell container to pin the gamete tail. An example is shown in FIG. 14.

Swiping across the gamete tail with the manipulation system can optionally be performed after pinning the gamete (e.g., with the same manipulation system) and/or at any other time. The swipe can be performed from the cut start point to the cut end point (e.g., wherein the tip of the needle travels from the cut start point to the cut end point), along the cut axis in the cut direction (e.g., wherein the bore of the needle is colinear with the cut axis), and/or otherwise performed relative to target immobilization points and/or target immobilization axes. The velocity of the manipulation system while swiping across the tail can be between 1 µm/sec-100 µm/sec (e.g., 10 µm/sec-30 µm/sec), but can alternatively be less than 1 µm/sec or greater than 100 µm/sec.

S730 can optionally include confirming successful gamete immobilization. S730 can be iteratively performed until successful gamete immobilization is confirmed, performed once, and/or otherwise performed. Confirming successful gamete immobilization preferably includes determining a gamete attribute value (e.g., using S300 methods; optionally performed after re-identification using S750 methods) and confirming gamete immobilization based on the gamete attribute values, but can be otherwise determined. For example, successful gamete immobilization can include the gamete attribute value satisfying one or more immobilization criteria. The immobilization criteria can be a motility attribute value (e.g., a gamete movement speed) equal to 0 and/or less than a motility threshold, a tail change metric (e.g., similarity score between the tail's encoding pre-immobilization and post-immobilization, wherein the similarity score can indicate nicking, severing, and/or any other physical damage to the tail), and/or any other immobilization criteria. In a specific example, the motility threshold can be between 0-20 µm/s or any range or value therebetween (e.g., 0.5 µm/s, 1 µm/s, 2 µm/s, 5 µm/s, 10 µm/s, etc.), but can alternatively be greater than 20 µm/s. However, gamete immobilization can be otherwise confirmed.

However, the gamete can be otherwise immobilized.

S700 can optionally include reidentifying the gamete S750. After an immobilization attempt, the gamete (S730) can be moved (e.g., out of the target region, away from the target position within the target region, out of the field of view, etc.), wherein the gamete is often no longer contacting the manipulation system. S750 can function to find the selected gamete (e.g., determine the gamete location) after an immobilization attempt. S750 can be performed after S730, iteratively with S730 (e.g., after each immobilization attempt), and/or at any other time.

S750 can include: determining a scene region for analysis and identifying the immobilized gamete within the scene region.

In a first variant, determining the scene region includes using manipulation system motion (e.g., actuation instructions, tracked manipulation system motion, etc.) to estimate an anticipated location of the gamete, wherein the scene region is determined based on the anticipated location. For example, the anticipated gamete location can be in the direction of the swiping motion of the manipulation system during an immobilization attempt (e.g., assuming the gamete travels in the cut direction). A trained model can optionally be used to determine the anticipated gamete location based on the manipulation system motion, wherein the training data includes previous immobilization attempts (e.g., previous swipe motions) and resulting gamete locations (e.g., wherein the model is trained to predict the resulting gamete location). The scene region can be centered at the cut end point, centered a predetermined distance away from the cut end point (e.g., further along the cut axis, assuming the gamete travels further than the swiping motion), be a region surrounding the manipulation system active end, and/or any other location based on the manipulation system motion. The method can optionally include searching increasingly large regions of the scene if the immobilized gamete is not found within the scene region.

In a second variant, determining the scene region includes using positioning system motion (e.g., actuation instructions) to estimate an anticipated location of the gamete, wherein the scene region is determined based on the anticipated location. For example, an anticipated gamete location can be determined based on current (post-immobilization) gamete motion (e.g., a gamete motility attribute value) and positioning system motion. The scene region can be centered at the anticipated gamete location, centered a predetermined distance away from the anticipated gamete location (e.g., in the direction of gamete motion and/or positioning system motion), and/or any other location based on the positioning system motion.

In a third variant, the scene region can be determined using any tracking methods in S200 (e.g., centered at an anticipated gamete location determined based on gamete motion).

In a fourth variant, the scene region is predetermined. In examples, the scene region can be the entire field of view, the target region, the manipulation region, and/or any other region.

However, the scene region can be otherwise determined.

The immobilized gamete can be reidentified (e.g., determining the location of the immobilized gamete) within the scene region for retrieval. The immobilized gamete is preferably reidentified based on the appearance of the selected gamete when the appearance features of a set of gamete components (e.g., the head, neck, etc.) substantially match between pre- and post-immobilization (e.g., based on a cosine distance, etc.), but can additionally or alternatively be reidentified based on expected changes in motion features, appearance features (e.g., tail appearance features), and/or based on any other set of features.

Figure 15:
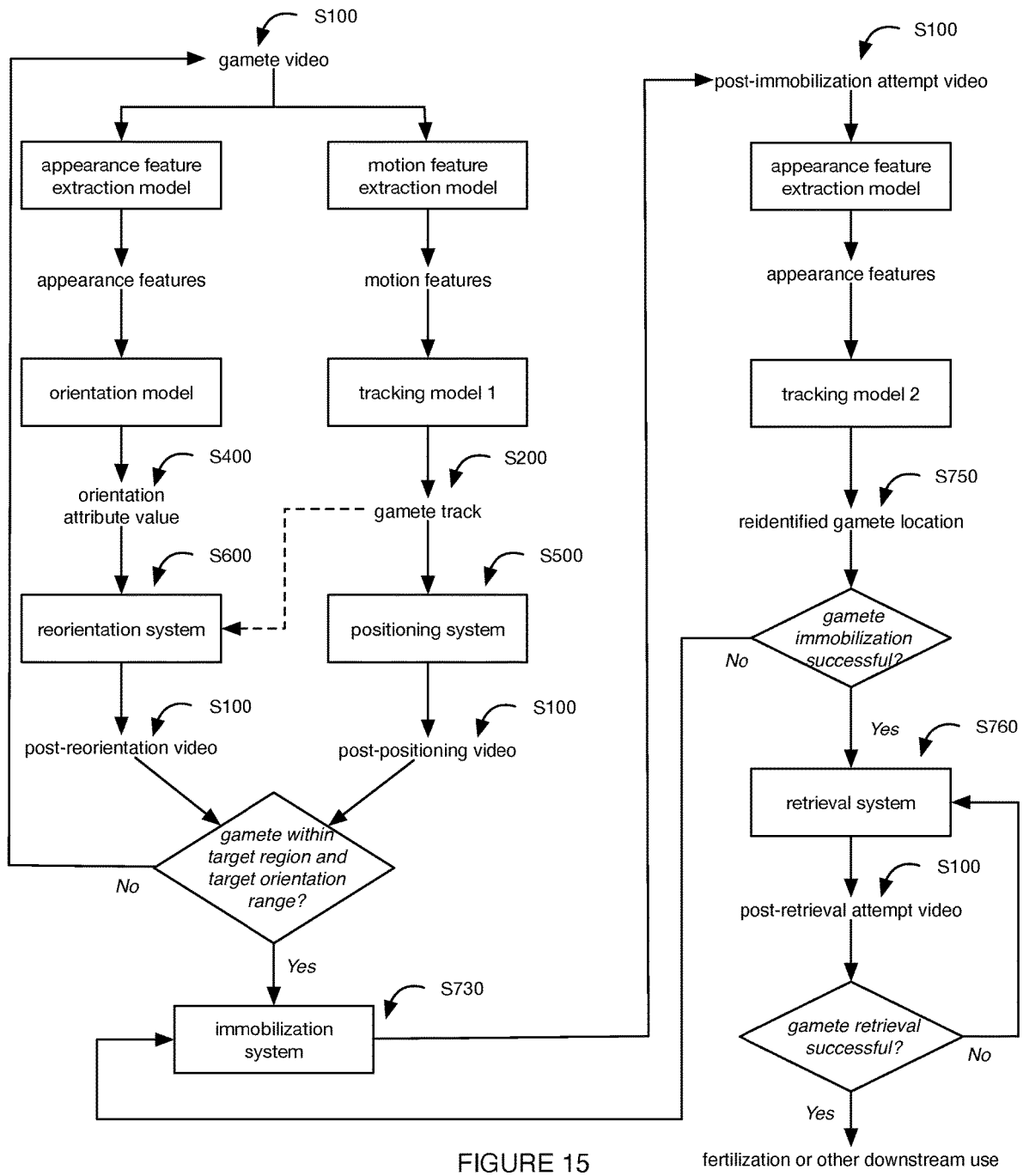
FIG. 15 depicts an example of the method, including reidentifying the gamete.

The immobilized gamete can be reidentified using the same tracking model used S200, a different tracking model, any other method in S200, and/or be otherwise performed. In a specific example, a first tracking model is used to match the gamete across frames pre-immobilization and a second tracking model is used to re-identify the gamete (the selected gamete) post-immobilization. An example is shown in FIG. 15. In specific examples, the first tracking model is based on motion features (e.g., not based on appearance features), based primarily on motion features (e.g., candidate gametes selected using motion features and the gamete is identified from the candidate gametes using appearance features; identified based on motion features and validates using appearance features; etc.), based on a combination of motion and appearance features, and/or based on any other inputs. In specific examples, the second tracking model is based on appearance features (e.g., not based on motion features), based primarily on appearance features (e.g., identified based on motion features and validated using a motility attribute value, wherein the motility attribute value can be compared to an anticipated post-immobilization motility attribute value), based on a combination of motion and appearance features, and/or based on any other inputs. In a specific example, after reidentification using the second tracking model, updated motility features can be extracted for the reidentified gamete (e.g., wherein the motility features are used to confirm immobilization) and/or the first tracking model can be used based on the updated motility features for the reidentified gamete (e.g., to continue to track the gamete post-immobilization, to confirm immobilization, etc.).

The tracking model can optionally use anticipated features for the gamete (e.g., wherein a candidate gamete is more likely to be selected when the candidate gamete features match the anticipated features, wherein the anticipated features are used to modify the tracking model or select a tracking model, etc.). In a first embodiment, the anticipated features include decreased gamete motility post-immobilization compared to pre-immobilization. In a first illustrative example, motion feature importance is downweighted when reidentifying the gamete post-immobilization (e.g., a tracking model is selected for post-immobilization that is not based on motion features; the same tracking model is used pre- and post-immobilization, but the motion feature weights are downweighted post-immobilization; etc.). In a second illustrative example, gametes are matched from a first frame pre-immobilization to gametes in a second frame post-immobilization based on the motion features, wherein the tracking model identifies the gamete with the greatest decrease in motility (e.g., identifying the gamete in both frames that does not have a motion feature match). In a second embodiment, the anticipated features include a change in tail morphology post-immobilization compared to pre-immobilization. In a first illustrative example, tail morphology feature importance is downweighted when reidentifying the gamete post-immobilization (e.g., a tracking model is selected for post-immobilization that is not based on tail morphology features; the same tracking model is used pre- and post-immobilization, but the tail morphology feature weights are downweighted post-immobilization; etc.). In a second illustrative example, gametes are matched from a first frame pre-immobilization to gametes in a second frame post-immobilization based on the appearance features, wherein the tracking model identifies the gamete with the greatest decrease in change in tail morphology (e.g., identifying the gamete in both frames that does not have a tail morphology feature match).

However, the gamete can be otherwise identified.

S700 can optionally include retrieving the gamete S760. S760 can function to isolate the gamete for additional processing (e.g., downstream ART processes). S760 can be performed after immobilizing the gamete (e.g., S730), after S760, performed without immobilizing the gamete, after S500, after S600, and/or any other suitable time. S760 can be performed using the manipulation system (e.g., the same manipulation system as S730, a different manipulation system, etc.) and/or any other suitable system.

Retrieving the gamete can include aspirating the gamete (e.g., using a micropipette, suction end effector, ICSI needle, any other aspirator, etc.), moving the gamete to a location in the container (e.g., a well), otherwise separating the gamete from the gamete sample, and/or any other retrieval method. The gamete can be aspirated from the tail tip, from the head, and/or from any other location on the gamete. Aspirating the gamete can optionally include a feedback system. For example, the suction force driving aspiration of the gamete can tuned for retrieval of the gamete in vicious fluid (e.g., with delayed feedback between adjusting the suction force and the resulting aspiration speed). In a specific example, a set of actuation instructions are provided to the aspiration system (e.g., controlling the suction force), wherein a delay period is implemented before adjusting the actuation instructions (e.g., increasing the suction force if the gamete is not moving into the aspirator). The delay period can be between 0.1s-5s or any range or value therebetween (e.g., 0.5s, 1s, 2s, 3s, 4s, etc.), but can alternatively be less than 0.1s or greater than 5s.

S760 preferably includes moving the manipulation system (e.g., a reference point on manipulation system such as the tip of an aspirator) to a retrieval location and/or retrieval orientation (e.g., a retrieval pose), but can alternatively include moving the gamete to the retrieval location and/or orientation (e.g., wherein the manipulation system remains stationary), moving both the manipulation system and the gamete, and/or not moving the manipulation system or the gamete. The retrieval location and/or orientation is preferably defined relative to the gamete, but can additionally or alternatively be defined relative to a field of view, the cell container, the scene, the manipulation system, a target region and/or a target position, and/or any other reference. For example, the retrieval location can be a predetermined distance from a gamete location (e.g., coordinates of the gamete tail center, tail tip, head center, etc.). The predetermined distance can be between 0 mm-10 mm or any range or value therebetween (e.g., 0.1 mm, 0.2 mm, 0.3 mm, 0.4 mm, 0.5 mm, 1 mm, 2 mm, 5 mm, etc.), but can alternatively be greater than 10 mm. The gamete location is preferably a gamete attribute value determined using S300 methods (e.g., based on images, videos, sub-videos, and/or a gamete track for the re-identified gamete from S750), but can alternatively be otherwise determined. In a specific example, the gamete location is an estimated tail tip location determined based on a gamete tail representation. In this example the gamete tail representation can optionally be a different gamete tail representation than the tail representation used in S730 to determine the target immobilization point and/or target immobilization axis (e.g., the tail representation used in S760 is a nonlinear function while the tail representation used in S730 is a linear function). The z-component of the gamete location can optionally be (e.g., estimated/assumed to be) the z-component the cell container base.

The z-component of the retrieval location can optionally be based on the cell container (e.g., raised a predetermined distance above the cell container to ensure the tail is not pinned; assuming that the immobilized gamete is located at the cell container bottom), based on a focus level (e.g., to ensure the gamete tail, the gamete head, and/or all or parts of the manipulation system is in focus), and/or any other suitable information. In a specific example, the retrieval location includes a predetermined distance above the cell container base, wherein the predetermined distance can be 0 mm-2 mm or any range or value therebetween (e.g., 0.05 mm, 0.1 mm, 0.2 mm, 0.3 mm, 0.4 mm, 0.5 mm, 1 mm, etc.), but can alternatively be greater than 2 mm. The retrieval location can optionally include a set of z-locations (e.g., with the same x and y locations), wherein S760 includes iteratively attempting retrieval at each z-location in the set (e.g., a z-direction aspiration sweep, with an optional delay between each aspiration attempt) until successful retrieval is confirmed.

In a first variant, the positioning system controls the gamete position in the x-direction, y-direction, and/or z-direction (e.g., via S500), and/or controls the gamete orientation (e.g., via S600) such that the gamete pose matches the retrieval pose, wherein the manipulation system can remain stationary during all or parts of the retrieval. In a second variant, the manipulation system is robotically actuated (e.g., in 2D, 3D, 4D, 5D, 6D, and/or any number of dimensions) to move the manipulation system (e.g., the tip of the aspirator) to the retrieval location and/or retrieval orientation relative to the gamete. In a third variant, a combination of the first and second variants are used. For example, the gamete position is controlled via the positioning system (e.g., via S500) to a target region (e.g., at or near the retrieval location), while the manipulation system is moved to the retrieval location (e.g., actuated in the z-direction to a z-component of the retrieval location) to retrieve the gamete.

S760 can optionally include confirming successful gamete retrieval (e.g., wherein S760 can be iteratively performed until successful gamete retrieval is confirmed). Confirming successful gamete retrieval preferably includes tracking the gamete within the aspirator post-retrieval (e.g., using S200 methods), but can alternatively include tracking the gamete elsewhere (e.g., in the cell container), confirming that the retrieved gamete moves with the aspirator, and/or not tracking the gamete. In specific examples, tracking the gamete within the aspirator can be useful for multi-gamete retrieval using the same aspirator. This confirmation can be based on one or more images and/or the video feed of the cell container (e.g., if the image no longer contains the gamete infer successful retrieval), based on one or more images and/or video of the manipulation system (e.g., if the image of the aspirator shows the gamete within the aspirator, infer successful retrieval), based on one or more images and/or video feed of a post-retrieval container (e.g., after retrieval, gametes are deposited in a separate container, where images can confirm successful retrieval), and/or based on any other suitable measurement.

Figure 19A:
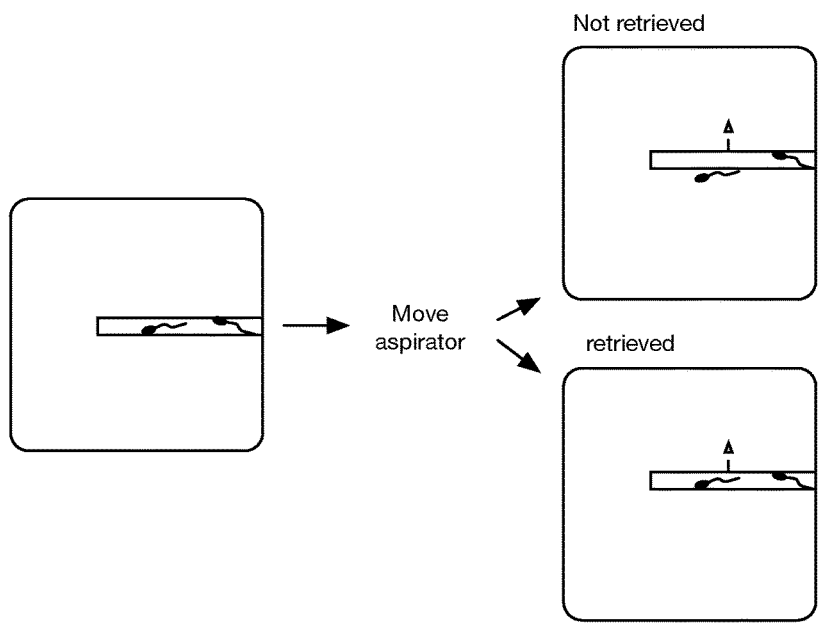
FIGS. 19A and 19B depicts a first and second example of confirming gamete retrieval.
Figure 19B:
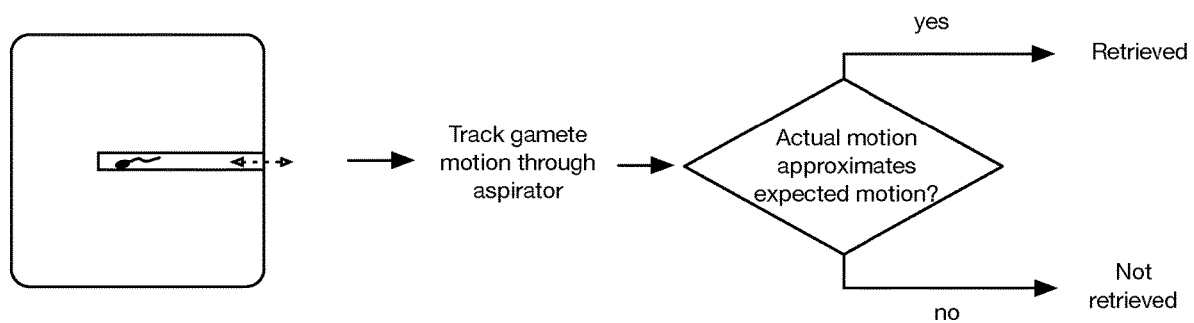

For example, manipulation system aspiration parameters (e.g., suction force, the aspirator location and/or motion, etc.) can be used to estimate an anticipated gamete location, wherein the retrieval confirmation is determined based on a comparison between the anticipated gamete location and the tracked gamete location. In a first specific example, the aspirator can apply positive and/or negative aspiration force (e.g., aspirating and/or ejecting) after the retrieval attempt such that the gamete is expected to move within the aspirator (e.g., moves up/down the aspirator bore; example shown in FIG. 19B). The amount of liquid aspirated and/or ejected can be between 1 femtoliters-100 µL or any range or value therebetween (e.g., 500 femtoliters-100 picoliters, 1000 femtoliters-10 picoliters, 1 nanoliter-10 µL, etc.), but can alternatively be less than 1 femtoliters or greater than 100 µL. In this example, confirmation of successful gamete retrieval can be based on the gamete track moving within the aspirator as expected (e.g., using S200 methods to track the gamete). In a second specific example, the aspirator can be moved (e.g., in the xy plane), wherein, confirmation of successful gamete retrieval can be based on the gamete track moving with the aspirator as expected (e.g., using S200 methods to track the gamete; example shown in FIG. 19A). In a third specific example, a combination of the first specific example and the second specific examples can be used (e.g., testing using the second specific example followed by testing using the first specific example). For example, if testing using the first specific example fails (e.g., the gamete does not move within the aspirator bore in response to aspiration/ejection), but testing using the second specific example succeeds (e.g., the gamete moves in coordination with the aspirator movement), the gamete can be stuck to the aspirator. The gamete can then be removed (e.g., by moving the aspirator, washing the aspirator, etc.) and the retrieval process repeated. However, gamete retrieval can be otherwise confirmed.

S760 can optionally include storing information about the retrieved gamete (e.g., gamete attribute values, time of immobilization, time of retrieval, images pre- or post-retrieval, etc.) in a database.

However, the gamete can be otherwise retrieved.

Different subsystems and/or modules discussed above can be operated and controlled by the same or different entities. In the latter variants, different subsystems can communicate via: APIs (e.g., using API requests and responses, API keys, etc.), requests, and/or other communication channels.

Alternative embodiments implement the above methods and/or processing modules in non-transitory computer-readable media, storing computer-readable instructions that, when executed by a processing system, cause the processing system to perform the method(s) discussed herein. The instructions can be executed by computer-executable components integrated with the computer-readable medium and/or processing system. The computer-readable medium may include any suitable computer readable media such as RAMs, ROMs, flash memory, EEPROMs, optical devices (CD or DVD), hard drives, floppy drives, non-transitory computer readable media, or any suitable device. The computer-executable component can include a computing system and/or processing system (e.g., including one or more collocated or distributed, remote or local processors) connected to the non-transitory computer-readable medium, such as CPUs, GPUs, TPUS, microprocessors, or ASICs, but the instructions can alternatively or additionally be executed by any suitable dedicated hardware device.

Embodiments of the system and/or method can include every combination and permutation of the various system components and the various method processes, wherein one or more instances of the method and/or processes described herein can be performed asynchronously (e.g., sequentially), contemporaneously (e.g., concurrently, in parallel, etc.), or in any other suitable order by and/or using one or more instances of the systems, elements, and/or entities described herein. Components and/or processes of the following system and/or method can be used with, in addition to, in lieu of, or otherwise integrated with all or a portion of the systems and/or methods disclosed in the applications mentioned above, each of which are incorporated in their entirety by this reference.

As a person skilled in the art will recognize from the previous detailed description and from the figures and claims, modifications and changes can be made to the preferred embodiments of the invention without departing from the scope of this invention defined in the following claims.

We claim:

1. A method, comprising:
   sampling a video of a gamete located within a scene;
   determining a gamete track across frames of the video;
   automatically positioning the gamete within a target region of the scene based on the gamete track;
   automatically immobilizing the gamete within the target region; and
   retrieving the immobilized gamete.

2. The method of claim 1, wherein the gamete is tracked using a first trained model, wherein the method further comprises: identifying a location of the immobilized gamete using a second trained model, wherein the immobilized gamete is retrieved based on the location of the immobilized gamete.

3. The method of claim 2, wherein the first trained model tracks the gamete based on motion features of the gamete, and wherein the second trained model identifies the location of the immobilized gamete based on appearance features of the gamete.

4. The method of claim 3, wherein the gamete is immobilized using a manipulation system, wherein the second trained model identifies the location of the immobilized gamete further based on motion of the manipulation system.

5. The method of claim 1, further comprising:
   generating a mask of a tail of the gamete based on the video; and
   determining a target immobilization point on the tail based on the mask, wherein immobilizing the gamete comprises contacting the gamete with a manipulation system at the target immobilization point.

6. The method of claim 5, further comprising:
   determining a target immobilization axis; and
   using the manipulation system to reorient gamete such that the gamete tail is within a threshold angular range relative to the target immobilization axis.

7. The method of claim 5, wherein generating the mask of the tail comprises:
   for each of a set of video frames, generating an intermediate mask of the tail based on the frame; and aggregating the intermediate masks of the tail across the set of video frames to generate the mask of the tail.

8. The method of claim 1, further comprising:
determining a linear representation of a tail of the gamete, wherein a target immobilization point is determined based on the linear representation of the tail, wherein immobilizing the gamete comprises contacting the gamete with a manipulation system at the target immobilization point;
determining a nonlinear representation of the tail; and
determining a target retrieval point on the tail based on the nonlinear representation of the tail, wherein the gamete is retrieved based on the nonlinear representation.

9. The method of claim 1, wherein the gamete is one of a set of gametes, the method further comprising:
determining an attribute value set for the gamete based on the video, using a trained machine learning model; and
selecting the gamete from the set of gametes using a trained selection model based on the attribute value set.

10. The method of claim 9, wherein the attribute value set comprises a timeseries attribute values.

11. The method of claim 1, further comprising fertilizing an ovum using the gamete.

12. A system, comprising:
an imaging system comprising a camera, wherein the imaging system is configured to sample a video of a gamete;
a processor configured to track the gamete across frames of the video;
a positioning system comprising an actuator, wherein the positioning system is configured to automatically position the gamete within a target region based on the gamete track in substantially real time; and
an aspirator positioned to retrieve the gamete from the target region.

13. The system of claim 12, wherein the positioning system further comprises a platform actuatable in at least three dimensions.

14. The system of claim 13, wherein the processor is further configured to determine a focus level based on the video using a trained focus model, wherein the positioning system is configured to automatically position the gamete further based on the focus level.

15. The system of claim 14, further comprising determining attention scores corresponding to frames of the video, wherein an attention score for a frame is positively correlated with the frame depicting a flat side of the gamete, wherein the processor is configured to determine the focus level further based on the attention scores.

16. The system of claim 12, wherein the aspirator is configured to iteratively aspirate at each of a set of z-locations until gamete retrieval is confirmed.

17. The system of claim 12, wherein the aspirator is further configured to immobilize the gamete within the target region.

18. The system of claim 17, wherein the processor is configured to track the gamete using a first trained model, wherein the processor is further configured to identify the location of the gamete post-immobilization using a second trained model, wherein the aspirator is configured to retrieve the gamete based on the location of the gamete post-immobilization.

19. The system of claim 18, wherein the first trained model is a motion model, and the second trained model is an appearance-based model.

20. The system of claim 12, wherein the gamete is retrieved for use in an assistive reproductive technology.

* * * * *